(12) United States Patent
Testi et al.

(10) Patent No.: US 8,703,749 B2
(45) Date of Patent: Apr. 22, 2014

(54) COMPOSITIONS AND METHODS FOR TREATING FRIEDREICH'S ATAXIA

(76) Inventors: Roberto Testi, Rome (IT); Ottaviano Incani, Sulmona (IT)

( * ) Notice: Subject to any disclaimer, the term of this patent is extended or adjusted under 35 U.S.C. 154(b) by 0 days.

(21) Appl. No.: 13/514,288

(22) PCT Filed: Dec. 7, 2010

(86) PCT No.: PCT/IB2010/003438
§ 371 (c)(1),
(2), (4) Date: Dec. 27, 2012

(87) PCT Pub. No.: WO2011/070444
PCT Pub. Date: Jun. 16, 2011

(65) Prior Publication Data
US 2013/0109658 A1    May 2, 2013

Related U.S. Application Data

(60) Provisional application No. 61/267,342, filed on Dec. 7, 2009, provisional application No. 61/332,146, filed on May 6, 2010.

(51) Int. Cl.
*A61K 31/63* (2006.01)

(52) U.S. Cl.
USPC .......................................... 514/155; 514/604

(58) Field of Classification Search
USPC .................................................. 514/155, 604
See application file for complete search history.

(56) References Cited

FOREIGN PATENT DOCUMENTS

| EP | 0129182 A1 | 12/1984 |
|---|---|---|
| EP | 1845083 A2 | 10/2007 |
| WO | WO 2007/112015 A2 | 10/2007 |

OTHER PUBLICATIONS

Dimmock et al. CAS: 107: 211450, 1987.*
Kendall, J.D. et al., "Synthesis, Biological Evaluation and Molecular Modelling of Sulfonohydrazides as Selective PI3K p110alpha Inhibitors," Bioorganic & Medicinal Chemistry, 2007, pp. 7677-7687, vol. 15.
PCT International Search Report, PCT Application No. PCT/IB2010/003438, Jul. 20, 2011, 18 pages.
Rai, M. et al., "HDAC Inhibitors Correct Frataxin Deficiency in a Friedreich Ataxia Mouse Model," PLOS One, Apr. 2008, pp. 1-61, vol. 3, No. 4.
Siemann, S. et al., "N-Arylsulfonyl Hydrazones as Inhibitors of IMP-1 Metallo-Beta-Lactamase," Antimicrobial Agents and Chemotherapy, Aug. 2002, pp. 2450-2457, vol. 46, No. 8.

* cited by examiner

*Primary Examiner* — Rei-tsang Shiao
(74) *Attorney, Agent, or Firm* — Fenwich & West LLP

(57) ABSTRACT

A method of treating Friedreich's Ataxia with compounds of formula I including pharmaceutically acceptable salts, tautomers or stereoisomers of compounds of formula Lp.

17 Claims, 15 Drawing Sheets

A

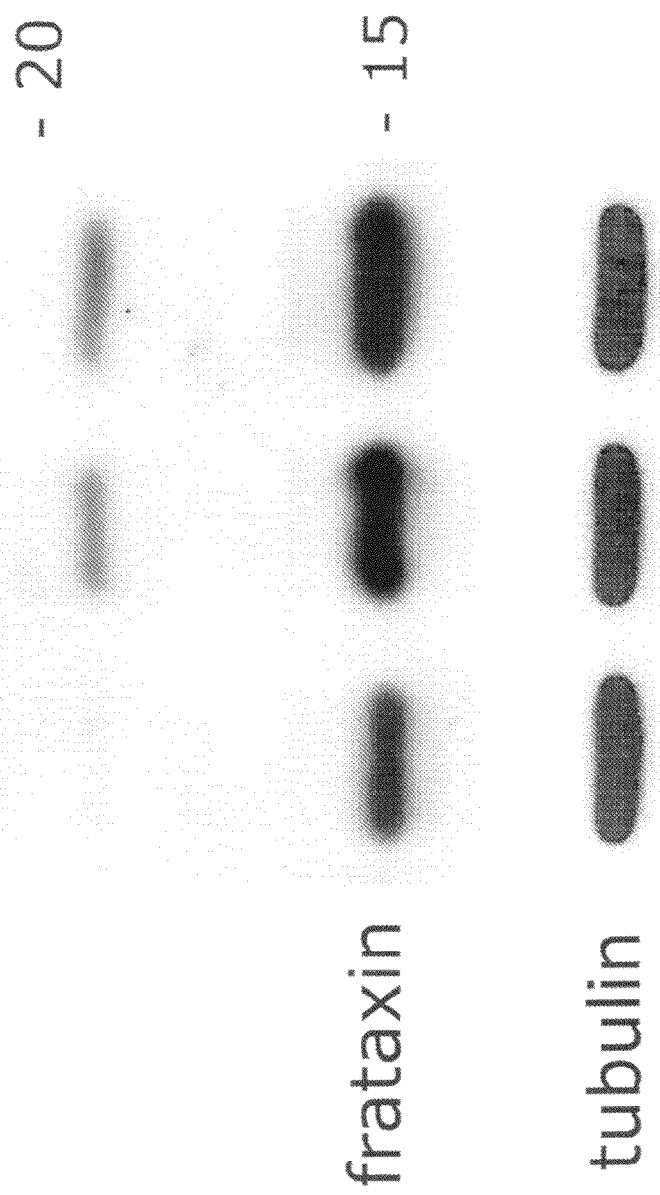

COMPOSITIONS AND METHODS FOR TREATING FRIEDREICH'S ATAXIA

RELATED APPLICATIONS

This application is the 35 USC 371 national stage entry of PCT/IB2010/003438 and claims the benefit of the filing date of U.S. App. No. 61/332,146 filed May 6, 2010 and U.S. App. No. 61/267,342 filed Dec. 7, 2009, both of which are hereby incorporated by reference for all purposes.

SEQUENCE LISTING

The instant application contains a Sequence Listing which has been submitted in ASCII format via EFS-Web and is hereby incorporated by reference in its entirety. Said ASCII copy, created on Jan. 20, 2011, is named 17407PCT_CRF sequencelisting.txt and is 26,905 bytes in size.

FIELD

The present invention relates generally to compositions and methods useful for the treatment of Friedreich's Ataxia.

BACKGROUND OF THE INVENTION

Friedreich's Ataxia (FRDA) affects >20.000 individuals in Caucasian populations. Generally within 10 to 15 from onset it leads to loss of deambulation and complete disability, with premature death often caused by cardiac insufficiency[1]. Symptoms usually appear late in the first decade or early in the second decade of life, and include gait instability and general clumsiness. Skeletal abnormalities, such as scoliosis or pes cavus, may be already present. Gait ataxia has both cerebellar and sensory features, involves truncus and limbs, and is progressive and generally unremitting. Swaying is common and, as it becomes more severe, eventually requires constant support and wheelchair use. Dysarthria occurs early in the disease and progress to complete speech impairment. Dysphagia is a late feature and may require artificial feeding. Ventricular hypertrophy characterizes the cardiac picture, and may progressively lead to congestive heart failure and fatal arrhythmias. A significant minority of patients also develop diabetes mellitus, by not yet clearly defined mechanisms[2].

FRDA is caused by homozygous hyperexpansion of GAA triplets within the first intron of the FXN gene, an highly conserved five-exon gene located on the long arm of human chromosome 9, coding for the protein frataxin. Pathological GAA expansions (from ~70 to >1,000 triplets) result in "sticky" DNA structures and epigenetic changes that severely reduce transcription of the FXN gene. FRDA patients live with 10-30% residual frataxin, the severity of the disease being directly proportional to the number of GAA triplets and to the consequent degree of frataxin reduction. A minority of FRDA patients, so called compound heterozygotes, has pathological GAA expansions on one FXN allele and loss-of-function mutations on the other. Complete loss of frataxin is not compatible with life, in all higher species examined[3].

Human frataxin is synthesized as a 210 amino acid (aa) precursor that is rapidly targeted to the mitochondria. Upon entrance into the mitochondria, the frataxin precursor undergoes a two-step proteolytic processing, mediated by the mitochondrial protein peptidase (MPP). The resulting mature frataxin is a 130aa globular polypeptide that mostly resides within the mitochondrial matrix[4,5], but that can be also found outside the mitochondria[6,7], where it might interact with and regulate cytosolic aconitase/IRP1[8]. Frataxin may bind iron directly and act either as an iron donor[9,10] or as an iron sensor involved in the proper functioning of the iron-sulphur cluster (ISC) machinery[11]. Frataxin-defective cells have reduced activity of ISC-containing enzymes, a general imbalance in intracellular iron distribution and increased sensitivity to oxidative stress.

There is currently no specific therapy to prevent the progression of the disease[12]. Most therapeutic approaches are aimed at reducing mitochondrial dysfunction and are based on the use of anti-oxidant or iron chelators[13,14]. Beside this, as levels of residual frataxin are crucial in determining the severity of the disease, many efforts have been put in the identification of molecules that increase frataxin transcription[15,16]. However, no studies have been so far reported regarding neither the physiological turnover of this protein in humans, nor any factors that can modulate its stability. Therefore, the comprehension of the molecular mechanisms that regulate frataxin protein stability might provide fundamental information towards the design of new therapeutic approaches.

Although the maturation process of frataxin has been well characterized, no information is available concerning the biology of frataxin degradation. Since the Ubiquitin-Proteasome System (UPS) is the major pathway for regulated intracellular protein degradation in higher eukaryotes, this pathway was investigated for its involvement in the control of frataxin turnover[17].

SUMMARY

Evidence is provided that the UPS regulates frataxin stability. Frataxin turnover can be modulated by proteasome inhibitors and $K^{147}$ was identified as the single lysine residue within frataxin that is responsible for its ubiquitination and degradation. Most importantly, by combining structure-based high-throughput virtual screening and experimental validation, a new class of compounds was identified that are able to interact with the $K^{147}$-harboring pocket, prevent frataxin ubiquitination, promote frataxin accumulation and correct functional defects in Friedreich's Ataxia cells. Increasing frataxin levels by interfering with frataxin ubiquitination is a method of treating Friedreich's Ataxia.

A first aspect provides a method of treating Friedrich's Ataxia, comprising administering to a subject a therapeutically effective amount of a compound of formula (I) or a pharmaceutically acceptable salt, tautomer or stereoisomer thereof:

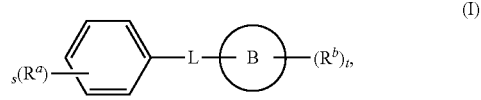

(I)

wherein:
L is a linking group selected from the group consisting of $-S(O)_2-NH-(CR_2)_x-$, $-S(O)_2-NH-N=(CR)-$ and $-S(O)_2-NH-C(O)-NH-(CR_2)_y-$
wherein:
R is H or $C_1$-$C_4$ alkyl, and
x and y are each independently 0, 1 or 2;
B is a 5- or 6-membered aromatic ring having 1 or 2 optional nitrogen heteroatoms;
each $R^a$ and $R^b$ is independently $C_1$-$C_6$ alkyl, $C_2$-$C_6$ alkenyl, $C_2$-$C_6$ alkynyl, $C_1$-$C_6$ alkoxy, halo, oxo, $-NO_2$, —$CF_3$, —CN, —$OR_9$, —$SR_9$, —$C(O)R_9$, —NHC(O)$R_9$, —$C(O)OR_9$, —$OC(O)R_9$, —$NR_{10}R_{11}$, —$C(O)NR_{10}R_{11}$, —$NHR_9C(O)NR_{10}R_{11}$, or —$SO_2NR_{10}R_{11}$, aryl, arylalkyl, cycloalkyl, or heterocycle, wherein:

$R_9$, $R_{10}$, and $R_{11}$ are independently H, $C_1$-$C_6$ alkyl, $C_2$-$C_6$ alkenyl, $C_2$-$C_6$ alkynyl, $C_1$-$C_6$ alkoxy, halo, aryl, arylalkyl, cycloalkyl, or heterocycle, each being optionally substituted with one to four substituents, and two $R^a$ or two $R^b$ together with the atoms to which they attach on the ring optionally form a ring;

s is 0, 1, 2 or 3; and t is 1, 2, 3 or 4.

In a first embodiment of the first aspect each $R^a$ is independently $C_1$-$C_6$ alkyl, halo, —$NO_2$, —$CF_3$, —CN, or —$OR_9$.

In a second embodiment of the first aspect, each $R^b$ is independently $C_1$-$C_6$ alkyl, halo, —$C(O)OR_9$, —$C(O)R_9$, —$NO_2$, —$CF_3$, —CN, or —$OR_9$.

In a third embodiment of the first aspect, L is —$S(O)_2$—NH—N=(CH)— and one of the two carbons on ring A ortho to the attachment to L is unsubstituted.

In a fourth embodiment of the first aspect, B is selected from the group consisting of a phenyl group, an imidazole, a pyridine and a pyrimidine.

In a fifth embodiment of the first aspect, the compound is of formula Ia:

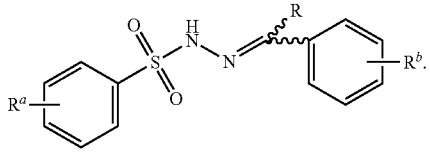

In a sixth embodiment of the first aspect, the compound is of formula Ib:

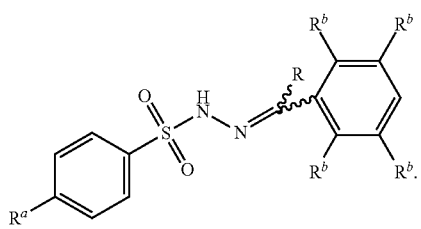

In a seventh embodiment of the first aspect, the compound is of formula Ic:

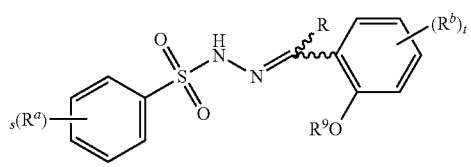

wherein t is 1, 2 or 3 and the other variables remain as defined with respect to formula I.

In an eighth embodiment of the first aspect, the compound has the structure of formula Id:

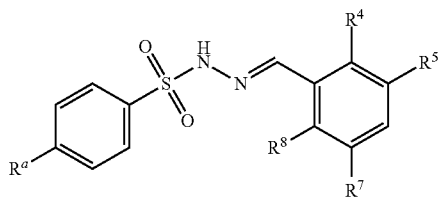

wherein $R^a$ is halo, $C_1$-$C_6$ alkyl, $C_1$-$C_6$ alkoxy, or —$NO_2$; $R^4$ and $R^8$ are independently H, —OH, or $C_1$-$C_6$ alkoxy; and $R^5$ and $R^7$ are independently H, halo, or —$NO_2$.

In a ninth embodiment of the first aspect at least one $R^b$ is —$NO_2$.

In a tenth embodiment of the first aspect t is 2 or 3 and at least one $R^b$ is a halogen and at least one $R^b$ is —$NO_2$.

In an eleventh embodiment of the first aspect, s is 1, 2 or 3 and at least one $R^a$ is a halogen.

In a twelfth embodiment of the first aspect, the compound has the structure of formula XII:

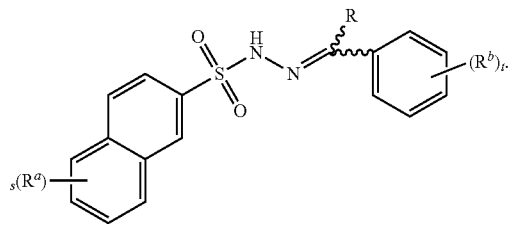

In a thirteenth embodiment of the first aspect, the method of treating Friedreich's Ataxia comprises inhibiting ubiquitination of frataxin.

In a fourteenth embodiment of the first aspect, the method of treating Friedreich's Ataxia comprises elevating intracellular frataxin levels.

A second aspect provides a method of elevating intracellular frataxin levels.

In a first embodiment of the second aspect, elevating intracellular frataxin levels is accomplished by inhibiting ubiquitination of frataxin.

In a second embodiment of the second aspect, elevating intracellular frataxin levels is accomplished by blocking binding by ubiquitin of lysine 147 of frataxin.

In a third embodiment of the second aspect the blocking of binding by ubiquitin of lysine 147 of frataxin is accomplished by a compound having the structure of formula I, Ia, Ib, Ic, Id or XII.

A third aspect provides a method of inhibiting the ubiquitination of frataxin, comprising blocking binding by ubiquitin of lysine 147 of frataxin, wherein frataxin has the sequence of SEQ ID NO:1.

In a first embodiment of the third aspect the blocking of binding by ubiquitin of lysine 147 of frataxin is accomplished by a compound having the structure of formula I, Ia, Ib, Ic, Id or XII.

A fourth aspect provides a method of identifying an agent that inhibits ubiquitination of frataxin thereby elevating the intracellular levels of frataxin, comprising the steps of: providing an agent; contacting the agent with frataxin or a fragment thereof; measuring a signal correlated with a lack of ubiquitination or a lack of frataxin degradation; and determining whether said agent inhibits ubiquitination of frataxin.

In a first embodiment of the fourth aspect, determining whether said agent inhibits ubiquitination of frataxin comprises measuring intracellular frataxin levels.

In a second embodiment of the fourth aspect, the method further comprises the step of designing an agent based upon a three-dimensional structure of a frataxin binding pocket defined by the structural coordinates of at least amino acid residues 92-106, 126-132, and 144-156 of native frataxin (SEQ ID: 1).

In a second embodiment of the fourth aspect, the three-dimensional structure of the frataxin binding pocket is determined using X-ray crystallography.

In a third embodiment of the fourth aspect, the three-dimensional structure of the frataxin binding pocket is determined using protein NMR.

In a fifth aspect of the invention, pharmaceutical compositions comprising a compound of one of structures I, Ia, Ib, Ic, Id or XII are provided.

BRIEF DESCRIPTION OF THE DRAWINGS

FIG. 9 illustrates additional compounds are effective in inducing frataxin accumulation in FRDA lymphoblasts.

DETAILED DESCRIPTION

Figure 1:
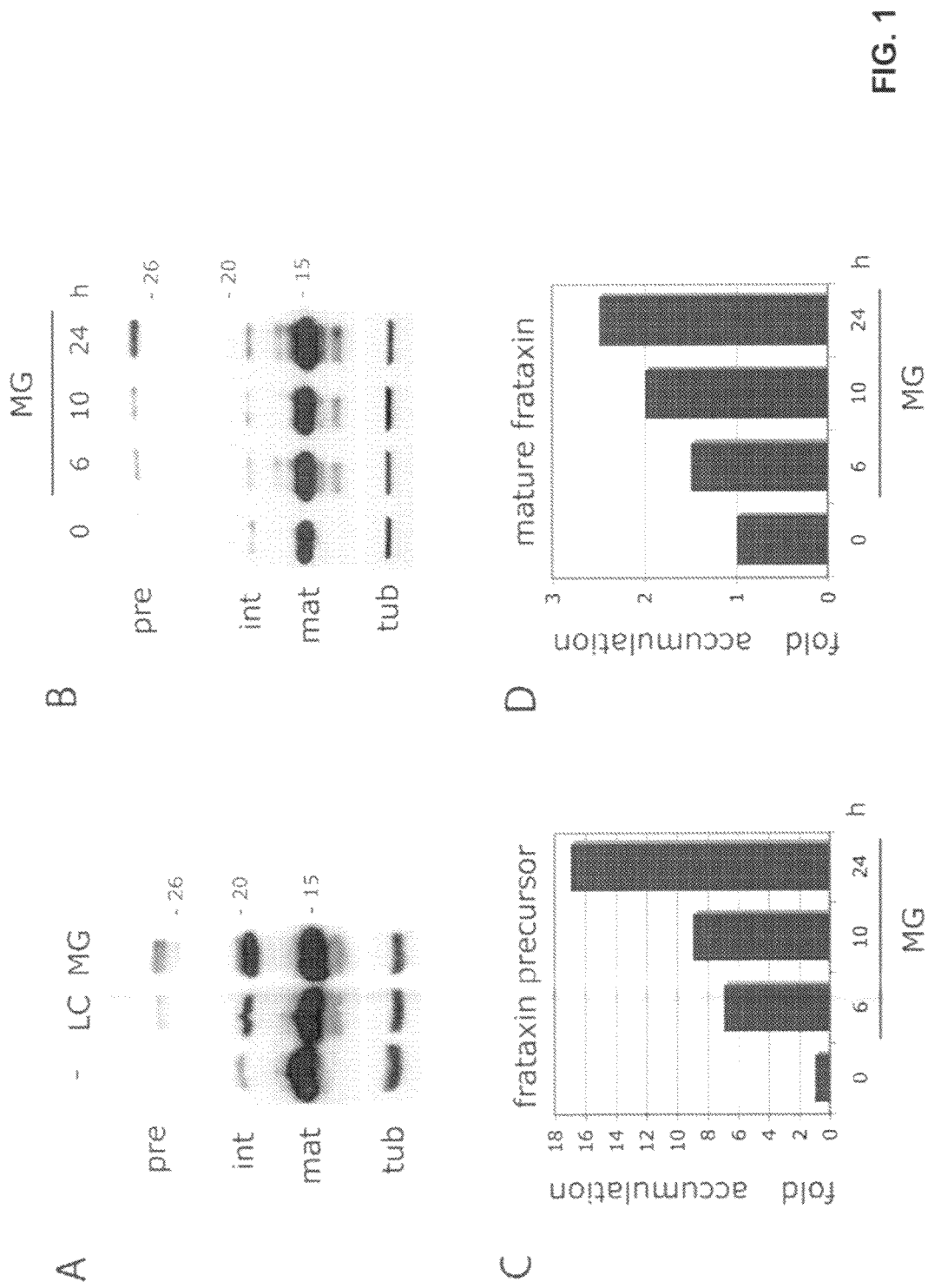
FIG. 1 illustrates that frataxin levels are controlled by proteasome-mediated degradataion.
Figure 1:
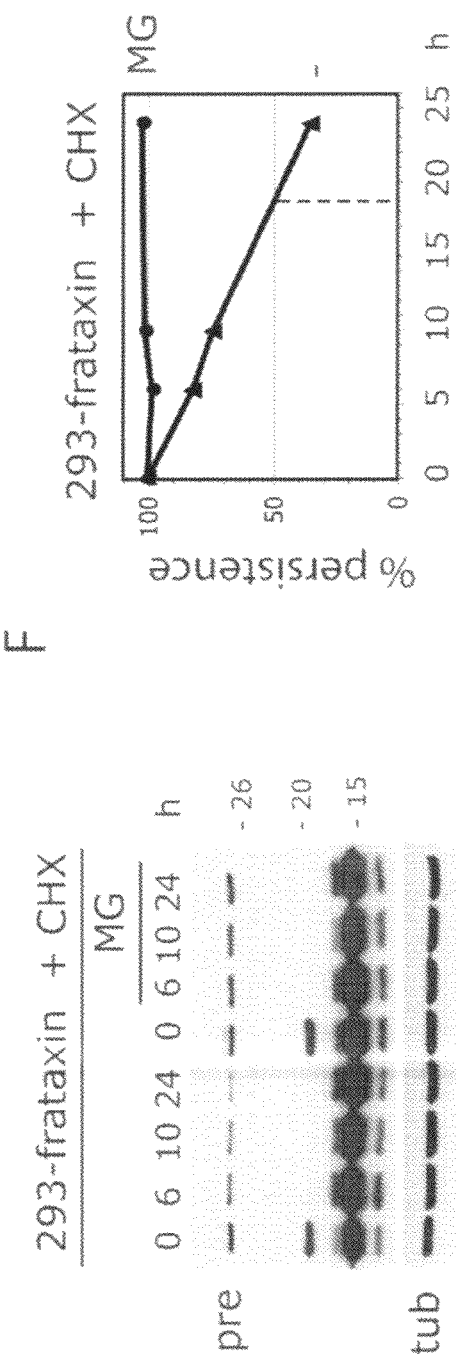
Figure 1:
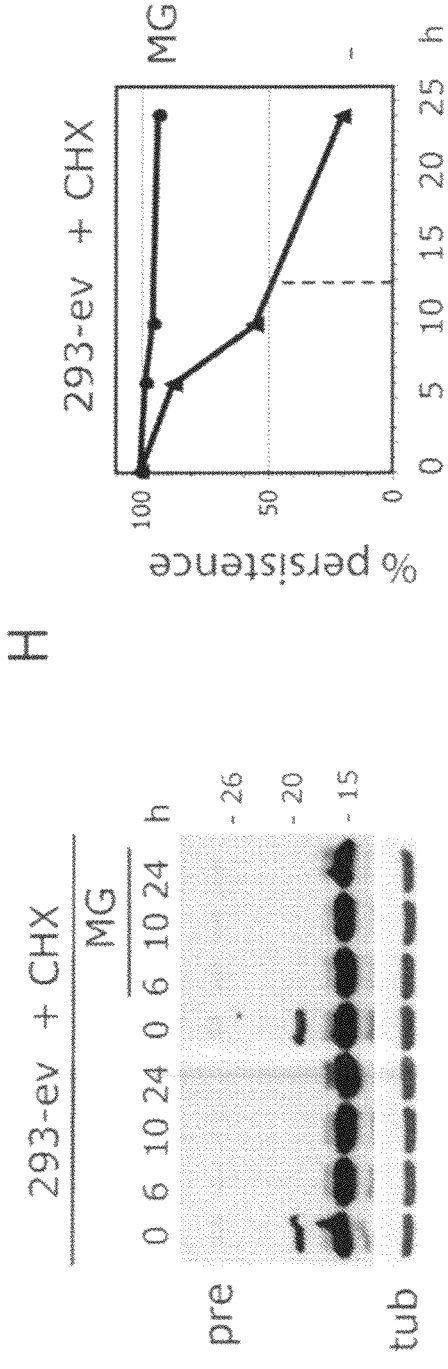

Described herein are compositions and methods for the treatment of Freidrich's Ataxia. The present disclosure relates to the surprising discovery that Freidrich's Ataxia can be treated by inhibiting degradation of frataxin by the Ubiquitin-Proteasome System. Frataxin is directly modified by ubiquitin, and lysine$^{147}$ is the critical residue responsible for frataxin ubiquitination and subsequent degradation.

Described herein are compounds and methods for treating Friedreich's Ataxia. In some aspects, methods of treating Friedreich's Ataxia are described, wherein the frataxin molecular pocket harboring lysine$^{147}$ is targeted. In further aspects, methods for inhibiting frataxin ubiquitination and degradation are described, wherein the molecular pocket harboring lysine$^{147}$ is targeted. In further aspects, methods for increasing frataxin levels are described, wherein the molecular pocket harboring lysine$^{147}$ is targeted.

The present disclosure describes for the first time the site of frataxin ubiquitination as the molecular pocket harboring lysine$^{147}$. In certain aspects, the present disclosure provides a description of the molecular pocket harboring lysine$^{147}$. In further aspects, methods of blocking ubiquitin from accessing the molecular pocket harboring lysine$^{147}$ are provided.

In certain aspects, compounds are provided for inhibiting ubiquitin-mediated degradation by targeting the frataxin molecular pocket harboring lysine$^{147}$. The compounds of the present disclosure may be any compound capable of inhibiting ubiquitin-mediated degradation of frataxin by targeting the molecular pocket harboring lysine$^{147}$. For instance, the compounds of the present disclosure may be small molecules, peptides, or any agent capable of targeting the molecular pocket. In further aspects, the compounds of the present disclosure are used to treat Friedreich's Ataxia by binding and blocking the frataxin molecular pocket harboring lysine$^{147}$. In further aspects, the compounds of the present disclosure are used to increase frataxin levels by binding and blocking the frataxin molecular pocket harboring lysine$^{147}$.

DEFINITIONS

Unless otherwise stated, the following terms used in this application, including the specification and claims, have the definitions given below. It must be noted that, as used in the specification and the appended claims, the singular forms "a," "an" and "the" include plural referents unless the context clearly dictates otherwise. Definition of standard chemistry terms may be found in reference works, including Carey and Sundberg (2007) "Advanced Organic Chemistry 5$^{th}$ Ed." Vols. A and B, Springer Science+Business Media LLC, New York. The practice of the present invention will employ, unless otherwise indicated, conventional methods of synthetic organic chemistry, X-ray crystallography, protein NMR, mass spectroscopy, protein chemistry, biochemistry, preparative and analytical methods of chromatography, recombinant DNA techniques and pharmacology, within the skill of the art.

Any terms not directly defined herein shall be understood to have the meanings commonly associated with them as understood within the art of the invention. Certain terms are discussed herein to provide additional guidance to the practitioner in describing the compositions, devices, methods and the like of aspects of the invention, and how to make or use them. It will be appreciated that the same thing can be said in more than one way. Consequently, alternative language and synonyms can be used for any one or more of the terms discussed herein. No significance is to be placed upon whether or not a term is elaborated or discussed herein. Some synonyms or substitutable methods, materials and the like are provided. Recital of one or a few synonyms or equivalents does not exclude use of other synonyms or equivalents, unless it is explicitly stated. Use of examples, including examples of terms, is for illustrative purposes only and does not limit the scope and meaning of the aspects of the invention herein.

The term "alkenyl" as used herein contemplates substituted or unsubstituted, straight and branched chain alkene radicals, including both the E- and Z-forms, containing from two to eight carbon atoms. The alkenyl group may be optionally substituted with one or more substituents selected from the group consisting of $C_1$-$C_6$ alkyl, $C_2$-$C_6$ alkenyl, $C_2$-$C_6$ alkynyl, $C_1$-$C_6$ alkoxy, halo, aryl, arylalkyl, cycloalkyl, or heterocycle.

The term "alkyl" as used herein contemplates substituted or unsubstituted, straight and branched chain alkyl radicals containing from one to fifteen carbon atoms. The alkyl group may be optionally substituted with one or more substituents selected from $C_1$-$C_6$ alkyl, $C_2$-$C_6$ alkenyl, $C_2$-$C_6$ alkynyl, $C_1$-$C_6$ alkoxy, halo, aryl, arylalkyl, cycloalkyl, or heterocycle.

The term "alkoxy" as used herein contemplates an oxygen with a $C_1$-$C_6$ alkyl group as a substituent and includes methoxy, ethoxy, butoxy, trifluoromethoxy and the like. It also includes divalent substituents linked to two separated oxygen atoms such as, without limitation, —O—(CH$_2$)$_{1-4}$—O—, —O—(CH$_2$)$_{1-4}$—O—(CH$_2$CH$_2$—O)$_{1-4}$— and —(O—CH$_2$CH$_2$—O)$_{1-4}$—.

The term "alkynyl" as used herein contemplates substituted or unsubstituted, straight and branched carbon chain containing from two to eight carbon atoms and having at least one carbon-carbon triple bond. The term alkynyl includes, for example ethynyl, 1-propynyl, 2-propynyl, 1-butynyl, 3-methyl-1-butynyl and the like. The alkynyl group may be optionally substituted with one or more substituents selected from C$_1$-C$_6$ alkyl, C$_2$-C$_6$ alkenyl, C$_2$-C$_6$ alkynyl, C$_1$-C$_6$ alkoxy, halo, aryl, arylalkyl, cycloalkyl, or heterocycle.

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. Typically, the antigen-binding region of an antibody will be most critical in specificity and affinity of binding.

The terms "aryl" as used herein contemplates substituted or unsubstituted single-ring and multiple aromatic groups (for example, phenyl, pyridyl and pyrazole, etc.) and polycyclic ring systems (naphthyl and quinolinyl, etc.). The polycyclic rings may have two or more rings in which two atoms are common to two adjoining rings (the rings are "fused") wherein at least one of the rings is aromatic, e.g., the other rings can be cycloalkyls, cycloalkenyls, aryl, heterocycles and/or heteroaryls. The aryl group may be optionally substituted with one or more substituents selected from C$_1$-C$_6$ alkyl, C$_2$-C$_6$ alkenyl, C$_2$-C$_6$ alkynyl, C$_1$-C$_6$ alkoxy, halo, aryl, arylalkyl, cycloalkyl, or heterocycle.

The term "arylalkyl" as used herein contemplates a C$_1$-C$_6$ alkyl group which has as a substituent an aromatic group, which aromatic group may be substituted or unsubstituted. The aralkyl group may be optionally substituted with one or more substituents selected from C$_1$-C$_6$ alkyl, C$_2$-C$_6$ alkenyl, C$_2$-C$_6$ alkynyl, C$_1$-C$_6$ alkoxy, halo, aryl, arylalkyl, cycloalkyl, or heterocycle.

The term "cycloalkyl" as used herein contemplates substituted or unsubstituted cyclic alkyl radicals containing from three to twelve carbon atoms and includes cyclopropyl, cyclopentyl, cyclohexyl and the like. The term "cycloalkyl" also includes polycyclic systems having two rings in which two or more atoms are common to two adjoining rings (the rings are "fused"). The cycloalkyl group may be optionally substituted with one or more substituents selected from C$_1$-C$_6$ alkyl, C$_2$-C$_6$ alkenyl, C$_2$-C$_6$ alkynyl, C$_1$-C$_6$ alkoxy, halo, aryl, arylalkyl, cycloalkyl, or heterocycle.

The term "halo" or "halogen" as used herein includes fluorine, chlorine, bromine and iodine.

The term "heterocycle" as used herein contemplates substituted or unsubstituted aromatic and non-aromatic cyclic radicals having at least one heteroatom as a ring member. Preferred heterocyclic groups are those containing five or six ring atoms which includes at least one hetero atom and includes cyclic amines such as morpholino, piperidino, pyrrolidino and the like and cyclic ethers, such as tetrahydrofuran, tetrahydropyran and the like. Aromatic heterocyclic groups, also termed "heteroaryl" groups, contemplates single-ring hetero-aromatic groups that may include from one to three heteroatoms, for example, pyrrole, furan, thiophene, imidazole, oxazole, thiazole, triazole, pyrazole, oxodiazole, thiadiazole, pyridine, pyrazine, pyridazine, pyrimidine and the like. The term heteroaryl also includes polycyclic heteroaromatic systems having two or more rings in which two or more atoms are common to two adjoining rings (the rings are "fused") wherein at least one of the rings is a heteroaryl, e.g., the other rings can be cycloalkyls, cycloalkenyls, aryl, heterocycles and/or heteroaryls. Examples of polycyclic heteroaromatic systems include quinoline, isoquinoline, cinnoline, tetrahydroisoquinoline, quinoxaline, quinazoline, benzimidazole, benzofuran, benzothiophene, benzoxazole, benzothiazole, indazole, purine, benzotriazole, pyrrolepyridine, pyrrazolopyridine and the like. The heterocyclic group may be optionally substituted with one or more substituents selected from the group consisting of C$_1$-C$_6$ alkyl, C$_2$-C$_6$ alkenyl, C$_2$-C$_6$ alkynyl, C$_1$-C$_6$ alkoxy, halo, aryl, arylalkyl, cycloalkyl, or heterocycle.

"Pharmaceutically acceptable salt" refers to a salt of a compound of the invention which is made with counterions understood in the art to be generally acceptable for pharmaceutical uses and which possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid and the like; or (2) salts formed when an acidic proton present in the parent compound is replaced by a metal ion, e.g., an alkali metal ion, an alkaline earth ion, or an aluminum ion; or coordinates with an organic base such as ethanolamine, diethanolamine, triethanolamine, N-methylglucamine, morpholine, piperidine, dimethylamine, diethylamine and the like. Also included are salts of amino acids such as arginates and the like, and salts of organic acids like glucurmic or galactunoric acids and the like (see, e.g., Berge et al., 1977, *J. Pharm. Sci.* 66:1-19).

"Specific binding" refers to the ability of two molecules to bind to each other in preference to binding to other molecules in the environment. Typically, "specific binding" discriminates over adventitious binding in a reaction by at least two-fold, more typically by at least 10-fold, often at least 100-fold. Typically, the affinity or avidity of a specific binding reaction, as quantified by a dissociation constant, is about $10^{-7}$ M or stronger (e.g., about $10^{-8}$ M, $10^{-9}$ M or even stronger).

A first aspect provides a method of treating Friedrich's Ataxia, comprising administering to a subject a therapeutically effective amount of a compound of formula (I) or a pharmaceutically acceptable salt, tautomer or stereoisomer thereof:

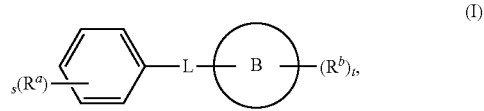

(I)

wherein:

L is a linking group selected from the group consisting of —S(O)$_2$—NH—(CR$_2$)$_x$—, —S(O)$_2$—NH—N═(CR)— and —S(O)$_2$—NH—C(O)—NH—(CR$_2$)$_y$— wherein:

R is H or C$_1$-C$_4$ alkyl, and x and y are each independently 0, 1 or 2;

B is a 5- or 6-membered aromatic ring having 1 or 2 optional nitrogen heteroatoms;

each R$^a$ and R$^b$ is independently C$_1$-C$_6$ alkyl, C$_2$-C$_6$ alkenyl, C$_2$-C$_6$ alkynyl, C$_1$-C$_6$ alkoxy, halo, oxo, —NO$_2$, —CF$_3$, —CN, —OR$_9$, —SR$_9$, —C(O)R$_9$, —NHC(O)R$^9$, —C(O)OR$_9$, —OC(O)R$_9$, —NR$_{10}$R$_{11}$, —C(O)NR$_{10}$R$_{11}$, —NHR$_9$C(O)NR$_{10}$R$_{11}$, or —SO$_2$NR$_{10}$R$_{11}$, aryl, arylalkyl, cycloalkyl, or heterocycle, wherein:

R$_9$, R$_{10}$, and R$_{11}$ are independently H, C$_1$-C$_6$ alkyl, C$_2$-C$_6$ alkenyl, C$_2$-C$_6$ alkynyl, C$_1$-C$_6$ alkoxy, halo, aryl, arylalkyl, cycloalkyl, or heterocycle, each being optionally substituted with one to four substituents, and two R$^a$ or two R$^b$ together with the atoms to which they attach on the ring optionally form a ring;

s is 0, 1, 2 or 3; and t is 1, 2, 3 or 4.

In a first embodiment of the first aspect each R$^a$ is independently C$_1$-C$_6$ alkyl, halo, —NO$_2$, —CF$_3$, —CN, or —OR$_9$.

In a second embodiment of the first aspect, each R$^b$ is independently C$_1$-C$_6$ alkyl, halo, —C(O)OR$_9$, —C(O)R$_9$, —NO$_2$, —CF$_3$, —CN, or —OR$_9$.

In a third embodiment of the first aspect, L is —S(O)$_2$—NH—N═(CH)— and one of the two carbons on ring A ortho to the attachment to L is unsubstituted.

In a fourth embodiment of the first aspect, B is selected from the group consisting of a phenyl group, an imidazole, a pyridine and a pyrimidine.

In a fifth embodiment of the first aspect, the compound is of formula Ia:

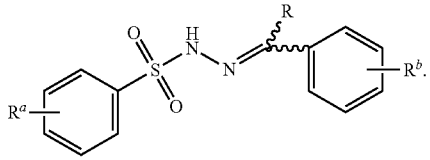

In a sixth embodiment of the first aspect, the compound is of formula Ib:

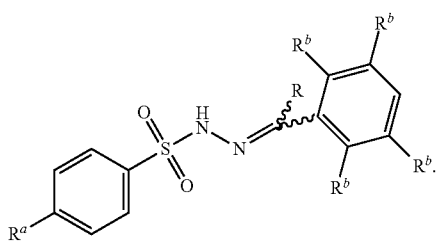

In a seventh embodiment of the first aspect, the compound is of formula Ic:

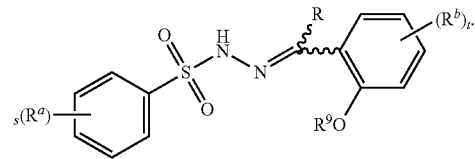

wherein t is 1, 2 or 3 and the other variables remain as defined with respect to formula I.

In an eighth embodiment of the first aspect, the compound has the structure of formula Id:

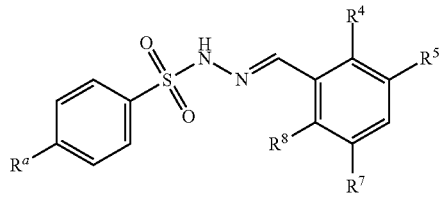

wherein R$^a$ is halo, C$_1$-C$_6$ alkyl, C$_1$-C$_6$ alkoxy, or —NO$_2$; R$^4$ and R$^8$ are independently H, —OH, or C$_1$-C$_6$ alkoxy; and R$^5$ and R$^7$ are independently H, halo, or —NO$_2$.

In a ninth embodiment of the first aspect at least one R$^b$ is —NO$_2$.

In a tenth embodiment of the first aspect t is 2 or 3 and at least one R$^b$ is a halogen and at least one R$^b$ is —NO$_2$.

In an eleventh embodiment of the first aspect, s is 1, 2 or 3 and at least one R$^a$ is a halogen.

In a twelfth embodiment of the first aspect, the compound has the structure of formula XII:

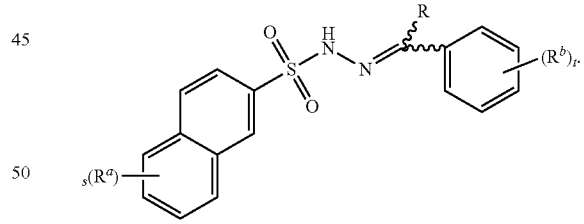

In an additional embodiment of the first aspect, the compound has the structure of formula XIII:

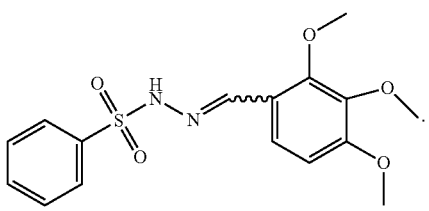 [SMILES: COc1ccc(C=NNS(=O)(=O)c2ccccc2)c(OC)c1OC]

Example compounds to be used with the disclosed methods have been identified through the screening methods disclosed herein. These compounds include:

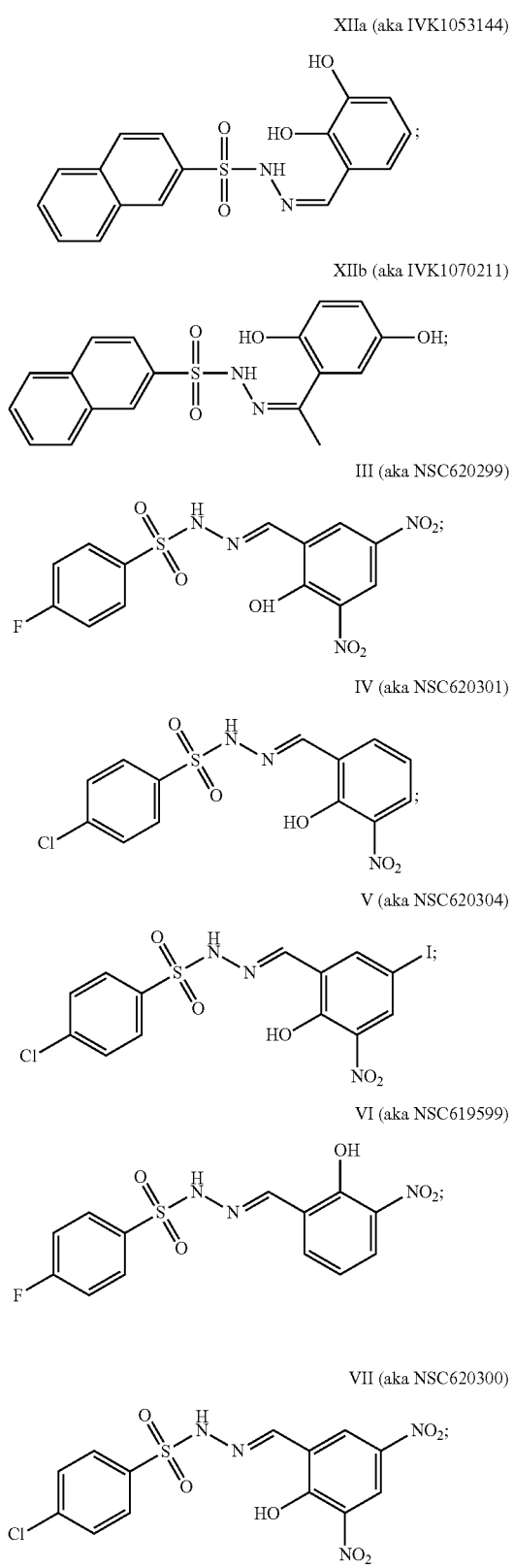

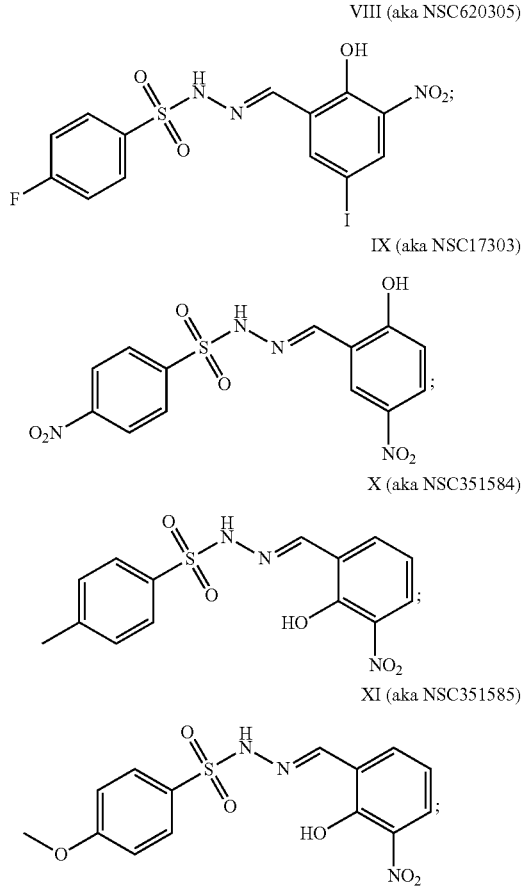

Numerous of the compounds useful in the disclosed methods undergo tautomerization. In those instances, the tautomers of the compounds are included within the scope compounds of disclosed formula I. In one example, a compound useful in the

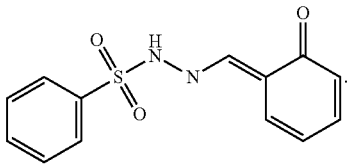 [SMILES: O=C1C=CC=C/C1=C\NNS(=O)(=O)c1ccccc1]

Its tautomer is:

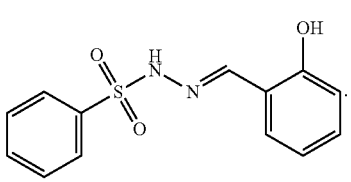 [SMILES: O=S(=O)(N/N=C/c1ccccc1O)c1ccccc1]

In a thirteenth embodiment of the first aspect, the method of treating Friedrich's Ataxia comprises inhibiting ubiquitination of frataxin.

In a fourteenth embodiment of the first aspect, the method of treating Friedreich's Ataxia comprises elevating intracellular frataxin levels.

A second aspect provides a method of elevating intracellular frataxin levels.

In a first embodiment of the second aspect, elevating intracellular frataxin levels is accomplished by inhibiting ubiquitination of frataxin.

In a second embodiment of the second aspect, elevating intracellular frataxin levels is accomplished by blocking binding by ubiquitin at lysine 147 of frataxin.

In a third embodiment of the second aspect the blocking of binding by ubiquitin of lysine 147 of frataxin is accomplished by any of the compounds of any of the formulae disclosed with respect to the first aspect A third aspect provides a method of inhibiting the ubiquitination of frataxin, comprising blocking binding by ubiquitin of lysine 147 of frataxin, wherein frataxin has the sequence of SEQ ID NO: 1.

In a first embodiment of the third aspect the blocking of binding by ubiquitin of lysine 147 of frataxin is accomplished by any of the compounds of any of the formulae disclosed with respect to the first aspect.

In some aspects, the compounds disclosed with respect to the first aspect inhibit ubiquitin-mediated degradation by binding and blocking the frataxin molecular pocket harboring lysine$^{147}$. In further aspects, these compounds are used to treat Friedreich's Ataxia by binding and blocking the frataxin molecular pocket harboring lysine$^{147}$. In further aspects, these compounds are used to increase frataxin levels by binding and blocking the frataxin molecular pocket harboring lysine$^{147}$.

A fourth aspect provides a method of identifying an agent that inhibits ubiquitination of frataxin, comprising the steps of: providing an agent; contacting the agent with frataxin or a fragment thereof; measuring a signal correlated with a lack of ubiquitination or a lack of frataxin degradation; measuring the elevation of intracellular frataxin levels; and determining whether said agent inhibits ubiquitination of frataxin.

In a first embodiment of the fourth aspect, determining whether said agent inhibits ubiquitination of frataxin comprises measuring intracellular frataxin levels.

In a second embodiment of the fourth aspect, the method further comprises the step of designing an agent based upon a three-dimensional structure of a frataxin binding pocket defined by the structural coordinates of at least amino acid residues 92-106, 126-132, and 144-156 of native frataxin (SEQ ID: 1).

In a third embodiment of the fourth aspect, the three-dimensional structure of the frataxin binding pocket is determined using X-ray crystallography.

In a fourth embodiment of the fourth aspect, the three-dimensional structure of the frataxin binding pocket is determined using protein NMR.

Pharmaceutical Compositions

In a fifth aspect of the invention, pharmaceutical compositions comprising a compound of one of structures of any one of the formulae disclosed with respect to the first aspect is provided.

The compounds described herein can be used as pharmaceutical compositions comprising the compounds, together with one or more pharmaceutically acceptable excipients or vehicles, and optionally other therapeutic and/or prophylactic ingredients. Such excipients include liquids such as water, saline, glycerol, polyethyleneglycol, hyaluronic acid, ethanol, cyclodextrins, modified cyclodextrins (i.e., sufobutyl ether cyclodextrins) etc. Suitable excipients for non-liquid formulations are also known to those of skill in the art. Pharmaceutically acceptable salts can be used in the compositions of the present invention and include, for example, mineral acid salts such as hydrochlorides, hydrobromides, phosphates, sulfates, and the like; and the salts of organic acids such as acetates, propionates, malonates, benzoates, and the like. A thorough discussion of pharmaceutically acceptable excipients and salts is available in *Remington's Pharmaceutical Sciences*, 18th Edition (Easton, Pa.: Mack Publishing Company, 1990).

Additionally, auxiliary substances, such as wetting or emulsifying agents, biological buffering substances, surfactants, and the like, may be present in such vehicles. A biological buffer can be virtually any solution which is pharmacologically acceptable and which provides the formulation with the desired pH, i.e., a pH in the physiologically acceptable range. Examples of buffer solutions include saline, phosphate buffered saline, Tris buffered saline, Hank's buffered saline, and the like.

Depending on the intended mode of administration, the pharmaceutical compositions may be in the form of solid, semi-solid or liquid dosage forms, such as, for example, tablets, suppositories, pills, capsules, powders, liquids, suspensions, creams, ointments, lotions or the like, preferably in unit dosage form suitable for single administration of a precise dosage. The compositions will include an effective amount of the selected drug in combination with a pharmaceutically acceptable carrier and, in addition, may include other pharmaceutical agents, adjuvants, diluents, buffers, etc.

The invention includes a pharmaceutical composition comprising a compound of the present invention including isomers, tautomers, racemic or non-racemic mixtures of isomers, or pharmaceutically acceptable salts or solvates thereof together with one or more pharmaceutically acceptable carriers, and optionally other therapeutic and/or prophylactic ingredients.

For solid compositions, conventional nontoxic solid carriers include, for example, pharmaceutical grades of mannitol, lactose, starch, magnesium stearate, sodium saccharin, talc, cellulose, glucose, sucrose, magnesium carbonate, and the like. Liquid pharmaceutically administrable compositions can, for example, be prepared by dissolving, dispersing, etc., an active compound as described herein and optional pharmaceutical adjuvants in an excipient, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents, tonicifying agents, and the like, for example, sodium acetate, sorbitan monolaurate, triethanolamine sodium acetate, triethanolamine oleate, etc. Actual methods of preparing such dosage forms are known, or will be apparent, to those skilled in this art; for example, see Remington's Pharmaceutical Sciences, referenced above.

For oral administration, the composition will generally take the form of a tablet, capsule, a softgel capsule or may be an aqueous or nonaqueous solution, suspension or syrup. Tablets and capsules are preferred oral administration forms. Tablets and capsules for oral use will generally include one or more commonly used carriers such as lactose and corn starch. Lubricating agents, such as magnesium stearate, are also typically added. When liquid suspensions are used, the active agent may be combined with emulsifying and suspending agents. If desired, flavoring, coloring and/or sweetening agents may be added as well. Other optional components for incorporation into an oral formulation herein include, but are not limited to, preservatives, suspending agents, thickening agents, and the like.

A pharmaceutically or therapeutically effective amount of the composition will be delivered to the subject. The precise effective amount will vary from subject to subject and will depend upon the species, age, the subject's size and health, the nature and extent of the condition being treated, recommendations of the treating physician, and the therapeutics or combination of therapeutics selected for administration. Thus, the effective amount for a given situation can be determined by routine experimentation. The subject may be administered as many doses as is required to reduce and/or alleviate the signs, symptoms, or causes of the disorder in question, or bring about any other desired alteration of a biological system.

The description of the aspects of the invention has been presented for the purpose of illustration; it is not intended to be exhaustive or to limit the invention to the precise forms disclosed. Persons skilled in the relevant art can appreciate that many modifications and variations are possible in light of the above teachings. It should be noted that the language used in the specification has been principally selected for readability and instructional purposes, and it may not have been selected to delineate or circumscribe the inventive subject matter. Accordingly, the disclosure of the aspects of the invention is intended to be illustrative, but not limiting, of the scope of the invention.

All references, issued patents and patent applications cited within the body of the specification are hereby incorporated by reference in their entirety, for all purposes.

EXAMPLES

Frataxin Binding Site Analysis.

The crystal structure of human frataxin[19,20] was employed to characterize regions of buried volume and to identify positions likely to represent binding sites based upon the size, shape, and burial extent of these volumes using the program PASS[21]. This analysis identified 8 putative binding sites, one of which, located around Lys 147, was used in the virtual screening and docking studies.

Target Preparation.

The virtual screening studies were performed with AutoDock version 4.2 and AutoDock Vina version 1[22]. For visual analysis MGLTools (http://mgltools.scripps.edu) and PyMOL (http://www.pymol.org/) were used. The crystallographic structure of frataxin from PDB file 1EKG, after removal of crystallization water molecules, was prepared adding polar hydrogens and calculating the atomic partial charges.

Library of Lead-Like Ligands.

The NCI database (http://dtp.nci.nih.gov), a library of about 250,000 compounds was used to identify small molecules capable of modulate frataxin stability preventing its ubiquitination. For this work the version of NCI database from ZINC[23] was used; ZINC database is available as 3D structures ready to be used in molecular docking experiments. The ZINC NCI compounds ("ncid" dataset), was filtered to prepare a smaller dataset of candidates. To this end, the subset obtained from cluster analysis (similarity threshold of 60%, "ncid_t60" cluster from ZINC, 9218 compounds), filtered to select lead-like compounds (ZINC subset "lead-like", about 316,000 compounds,[24]), produced a relatively small dataset of 6,025 structures. These molecules were used in the virtual screening procedure.

Virtual Screening.

The dataset prepared from ZINC/NCI database was used with AutoDock Vina[22] to perform virtual screening experiments on the K147 site of frataxin. A cubic grid centered on the Cα of K147 with an edge of 22.5 Å was used. The screening of the dataset was performed with the structure of the protein kept fixed. The 100 top-ranked structures were analyzed. One of these compound was used to retrieve similar NCI compounds non included in the t60 cluster. Using the SMARTS (http://www.daylight.com/dayhtml/doc/theory/theory.smarts.html) query "O[A][A]C=NNS[c]", 87 compounds were retrieved from the NCI database (all compounds in subset "ncid" from ZINC). These molecules were again docked on the frataxin structures and finally, ~40 molecules were selected for in vitro testing. In the second-generation screening, the flexibility of selected side-chains of the binding site was treated as flexible to take into account for induced fitting effects.

Small Molecule Screening Assays.

To test small molecule candidates, HEK-293 cells were transiently transfected with frataxin-GFP fusion protein, using the Ca/Ph precipitation method in 10 cm plates. After 18 hrs, cells were splitted, pooled and plated again in 96 wells, to normalize for variation in transfection efficiency. Each molecule was then added at 50 or 100 μM to 12 independent wells. MG132 was used as a positive control. 18 hrs after treatment, cells from all wells were collected and pooled together. Cells were then fixed in 4% paraformaldehyde and changes in fluorescence intensity were monitored by FACS analysis. Small molecules increasing fluorescence intensity, similarly to MG132, were re-tested for their effects on both GFP alone and frataxin-GFP to identify molecules specifically affecting frataxin levels.

Cell Culture and Transfections.

Human embryonic kidney HEK-293 cells and Hela cells were maintained in DMEM supplemented with 10% FBS. HEK-293 were transfected with the calcium/phosphate precipitation method, using 20 μg total DNA (10 μg pIRES-frataxin and 10 μg HA-Ub, or corresponding empty vectors) on 10 cm dishes. Hela cells were transfected using Lipofectamine 2000 reagents (Invitrogen), according to manufacturer's instructions. Where indicated, the day after transfection, cells were treated for 16 h with 10 μM proteasome inhibitors, MG132 or Lactacystin, or 50 ng/ml DUB inhibitor Ubiquitin-Aldehyde. Flp-In-HEK-293 cells (Invitrogen) are HEK-293 variants allowing the stable and isogenic integration and expression of a transfected gene. Flp-In-HEK-293 cells were maintained in DMEM supplemented with 10% FBS and transfected with the calcium/phosphate precipitation method. Briefly, cells were plated on 10 cm dishes and transfected with 10 μg total DNA. The HEK-293 clone stably expressing frataxin$^{1-210}$ was previously described (4). The HEK-293 clone stably expressing frataxin$^{K147R}$ was obtained from cultures in selection medium containing 100 μg/ml hygromycin B (Invitrogen). FRDA lymphoblasts GM15850, GM16798 and GM16241, as well control lymphoblasts GM15851, GM16241 and GM16215, were maintained in RPMI supplemented with 15% FBS. Treatments with specific ubiquitin-competing molecules were performed in 20% FBS containing medium. FRDA fibroblasts GM03816 were maintained in DMEM supplemented with 15% FBS.

Antibodies.

The following antibodies were used for immunoprecipitation and western blot analysis: mAb anti-frataxin (MAB-10876, Immunological Science), mAb anti-HA (clone HA-7, Sigma), mAb anti-Ubiquitin (clone P4D1, Santa Cruz), mAb anti-tubulin (Sigma), secondary antibody HRP-conjugated goat anti-mouse (Pierce). The following antibodies were used for FACS staining: mAb anti-frataxin (MAB-10485, Immunological Science), mAb anti-Bcl2 (sc-509, Santa Cruz), FITC-conjugated goat anti-mouse IgG/IgM (BD Bioscience Pharmingen).

Chemicals.

Proteasome inhibitors: MG132 and Lactacystin (Sigma Aldrich); DUB inhibitors: Ub-Aldehyde (Biomol) and N-Ethylmaleimide (NEM, Sigma Aldrich). Protein synthesis inhibitor: Cycloheximide (Sigma Aldrich).

DNA Constructs.

The pIRES2-frataxin$^{1-210}$ construct was previously described (Condo, I. et al., 2006). All the lysines mutants constructs were generated using the Quick-Change site-directed mutagenesis kit (Stratagene) with specific primers using pIRES2-frataxin$^{1-210}$ as template. All the constructs generated were verified by DNA sequencing. The Ha-Ub construct was generated by M. Treier in Dirk Bohmann's lab (Treier, M. et al. 1994). The pEGFP-frataxin construct was generated from pIRES2-frataxin$^{1-210}$ by PCR amplification with specific oligonucleotides designed to subclone the fragment into pEGFP-NI, to express a fusion product in frame with the N-terminus of GFP.

Immunoblotting and Immunoprecipitation.

Cell extracts were prepared in modified RIPA buffer (10 mM sodium phosphate pH7.2, 150 mM NaCl, 1% Na deoxycholate, 0.1% SDS, 1% Np40, 2 mM EDTA) or IP buffer (50 mM Tris-HCl, pH 7.5, 150 mM NaCl, 1% Nonidet P-40, 5 mM EDTA, 5 mM EGTA) supplemented with Complete protease inhibitor cocktail and 2 mM N-Ethylmaleimide (NEM). For immunoblotting, 100 µg of protein extract were separated on 12% SDS-PAGE, blotted onto nitrocellulose membrane and detected with specific antibodies. For in vivo detection of ubiquitin-conjugates 100 MG132 and 50 ng/ml Ubiquitin-Aldehyde were added to the lysis buffer. For immunoprecipitation, 5 mg of total protein extract prepared as above were incubated for 1-2 h at 4° C. with specific antibodies, previously conjugated to Protein G-sepharose (GE Healthcare). Immunocomplexes were then resolved and analysed by SDS-PAGE. All immunoblots were revealed by ECL (GE Healthcare). Densitometric analysis was performed using ImageJ software.

Flow Cytometric Analysis Offrataxin Levels.

Cells were collected after the indicated treatments and fixed for 20 minutes in 4% paraformaldehyde at room temperature. Cells were then permeabilized and blocked in a blocking solution (3% FBS in PBS) containing 0.2% Triton, for 1 hour at room temperature. Cells were then incubated overnight at 4° C. with anti-frataxin monoclonal antibody (MAB-10485, Immunological Science) or anti-Bcl2 monoclonal antibody (sc-509, Santa Cruz) diluted 1:200 in blocking solution. Cells were then washed 3 times in PBS and incubated for 1 hour at room temperature with FITC-conjugated goat anti-mouse IgG/IgM (BD Bioscience Pharmingen) diluted 1:200 in blocking solution. After washing 3 times with PBS cells were analyzed by flow cytometry (Becton Dickinson).

Aconitase Assay and Determination of ATP.

FRDA lymphoblasts and fibroblasts were washed twice with ice-cold Dulbecco's Phosphate Buffered Saline (DPBS) and lysed in CelLytic M buffer (Sigma-Aldrich) supplemented with Complete protease inhibitor cocktail, EDTA-free (Roche). Aconitase activity was measured spectrophotometrically at 340 nm by a coupled reaction of aconitase and isocitrate dehydrogenase. The assay reactions contained 100 mg of cell extract in 50 mM Hepes pH 7.4, 1 mM sodium citrate, 0.6 mM $MnCl_2$, 0.2 mM $NADP^+$ and 2 U/ml isocitrate dehydrogenase (Sigma-Aldrich). Citrate synthase activity was assessed using 10 mg of cell extract with the Citrate Synthase Assay Kit (Sigma-Aldrich CS0720). The aconitase activities were normalized with respect to citrate synthase ratios; one milliunit of enzyme was defined as the amount of protein that converted 1 nmol of $NADP^+$ in 1 min at 25° C. The intracellular ATP content was measured in black microtiter plates using 50 mg of cell extract with the ATP Bioluminescence Assay Kit CLS II (Roche) according to the manufacturer's protocol.

Frataxin Levels are Controlled by Proteasome-Mediated Degradation.

HeLa cells were transiently transfected with frataxin$^{1-210}$. 24 h after transfection cells were treated for 18 h with 10 µM of the indicated proteasome inhibitors. Total cell extracts were analysed by SDS-PAGE and revealed by immunoblotting with anti-frataxin antibody (upper panel) or anti-tubulin (lower panel). One representative experiment out of three performed with similar results is shown in FIG. 1A. LC: Lactacystin, MG: MG132. Pre: precursor; int: intermediate; mat: mature; tub: tubulin.

HEK-293 Flp-In cells stably transfected with frataxin$^{1-210}$ were treated for the indicated times with 10 µM MG132. Total cell extracts were blotted as in A. One representative experiment out of four performed with similar results is shown in FIG. 18.

FIGS. 1C and 1D show quantitative analysis of frataxin precursor and mature accumulation upon MG132 treatment of HEK-293 Flp-In cells, as shown in 1B.

HEK-293 Flp-In cells stably transfected with frataxin$^{1-210}$ (FIG. 1E) or empty vector (FIG. 1G) were treated for the indicated times with 100 µg/ml cycloheximide (CHX) in the presence or absence of 10 µM MG132 (MG). Total cell extracts were analysed by SDS-PAGE and revealed by immunoblotting with anti-frataxin antibody or anti-tubulin. One representative experiment out of five performed with similar results is shown. Pre: precursor, tub: tubulin.

FIGS. 1F and 1H illustrate densitometric analysis of the expression of frataxin precursor as shown in E and G, respectively, normalized to tubulin levels. Dotted line indicates frataxin precursor half-life.

Upon biosynthesis, the frataxin$^{1-210}$ precursor is rapidly imported in the mitochondrial matrix, where it is quantitatively processed to generate mature frataxin$^{81-210}$ $^{4,5}$ Since proteins within the mitochondrial matrix are shielded from UPS degradation, whether the UPS could affect the stability of the frataxin precursor was determined. To address this question, the proteasome in HeLa cells, transiently transfected with frataxin$^{1-210}$ to allow for sufficient precursor accumulation was inhibited. FIG. 1A shows that cells treated with proteasome inhibitors lactacystin (LC) or MG132 (MG) accumulated significantly higher amounts of precursor compared to untreated cells. To analyze the effect of proteasome inhibitors in further detail, HEK-293 Flp-In cells stably expressing frataxin$^{1-210}$ were used. This cell line is engineered to integrate a single copy of the transfected cDNA and therefore, unlike transiently transfected cells, it allows the accumulation of frataxin products at more physiologic levels. When these cells were treated with MG132, a time-dependent and quite remarkable (>15 fold after 24 hrs) accumulation of the frataxin precursor was observed. Most importantly, a ~2.5 fold accumulation of mature frataxin was also detected after 24 hrs of treatment (FIG. 1B-D).

The above data strongly suggest that a significant fraction of the frataxin precursor is constitutively targeted to UPS degradation. To better characterize this process, whether proteasome inhibition can modulate frataxin half-life was analyzed. HEK-293 Flp-In cells stably expressing frataxin$^{1-210}$ were treated with cycloheximide (CHX) to block new protein synthesis and the fading of the frataxin precursor was monitored in the presence of proteasome inhibitor MG132. FIG. 1E shows that the time-dependent degradation of the frataxin precursor is blocked by MG132. In these experimental conditions, the estimated half-life of frataxin precursor is approximately 18 hours (FIG. 1F). Most importantly, proteasome inhibition also prevents the degradation of the endogenous frataxin precursor (FIG. 1G), which shows an apparent half-life of 12 hours (FIG. 1H).

Frataxin can be Mono- and Poly-Ubiquitinated In Vivo.

Figure 2:
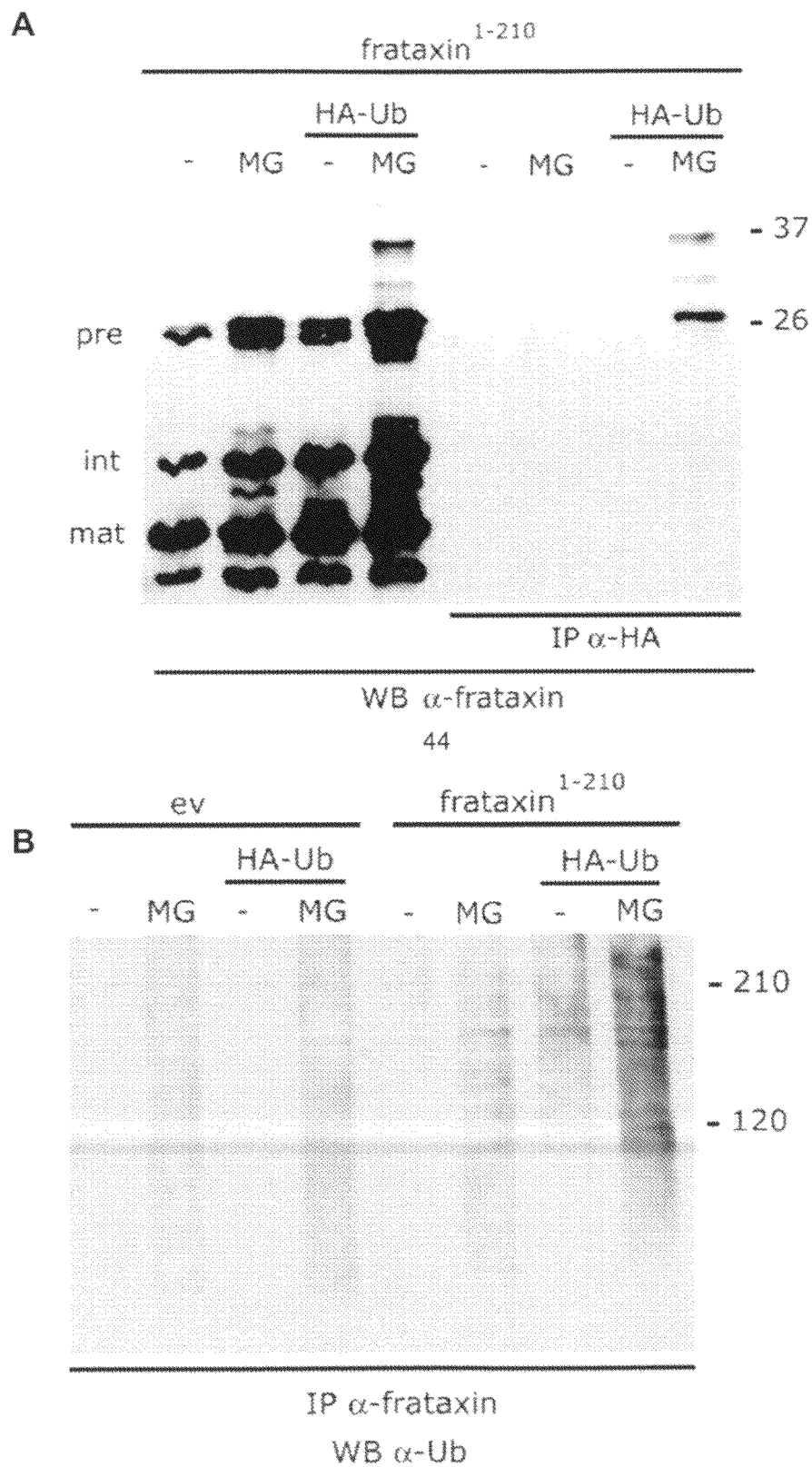
FIG. 2 illustrates that frataxin can be mono- and poly-ubiquitinated in vivo.

FIG. 2A illustrates HEK-293 cells transiently transfected with frataxin$^{1-210}$ and HA-tagged ubiquitin (HA-Ub) (where indicated) were treated with 10 μM MG132 (MG) for 16 h. One representative experiment out of five performed with similar results is shown. Total cell extracts (lanes 1-4) or anti-HA immunoprecipitates (lanes 5-8) were analyzed by WB with anti-frataxin antibody. Pre: precursor; int: intermediate; mat: mature frataxin.

FIG. 2B illustrates HEK-293 cells transiently transfected with frataxin$^{1-210}$ and HA-Ub (where indicated) or control empty vector (ev) were treated as above. Polyubiquitin-conjugated forms of frataxin were detected by WB with anti-ubiquitin antibody on immunoprecipitated frataxin. One representative experiment out of three performed with similar results is shown.

Protein degradation through the proteasome is a highly specific process that implies as a first step the conjugation of one or more ubiquitin molecules to the protein to be degraded. To address whether frataxin could be directly modified by ubiquitin, HEK-293 cells were transiently co-transfected with frataxin$^{1-210}$ and HA-tagged ubiquitin (HA-Ub), in the presence of MG132. FIG. 2A shows that, when HA-Ub is co-transfected with frataxin$^{1-210}$, and only in the presence of MG132, bands migrating slower than the precursor are recognized by anti-frataxin mAbs, consistent with the accumulation of mono-ubiquitinated frataxin amid proteasome inhibition (lane 4). When HA-Ub was immunoprecipitated and WB probed with anti-frataxin mAbs the same discrete slower-migrating bands were observed in co-transfected cells treated with MG132, indicating that proteasome inhibition allows the accumulation and detection of mono-ubiquitinated frataxin (lane 8).

Conversely, when frataxin was immunoprecipitated from HEK-293 cells transiently co-transfected with frataxin$^{1-210}$ and HA-tagged ubiquitin (HA-Ub), and WB probed with anti-Ub mAb, a ubiquitin smear was observed in cells treated with MG132, indicating that proteasome inhibition allows the accumulation and detection also of poly-ubiquitinated frataxin (FIG. 2B, lane 8). Importantly, immunoprecipitation of endogenous frataxin as well, from HEK-293 cells transfected with empty vector (ev), allowed the detection of poly-ubiquitinated frataxin in the presence of MG132 (FIG. 2B, lanes 2 and 4), suggesting that also endogenous frataxin can be directly modified by ubiquitin. Together these results indicate that frataxin can be mono- and polyubiquitinated in vivo and that the accumulation of ubiquitinated frataxin can be detected by blocking the proteasome.

$K^{147}$ is the Main Ubiquitination Target.

Figure 3:
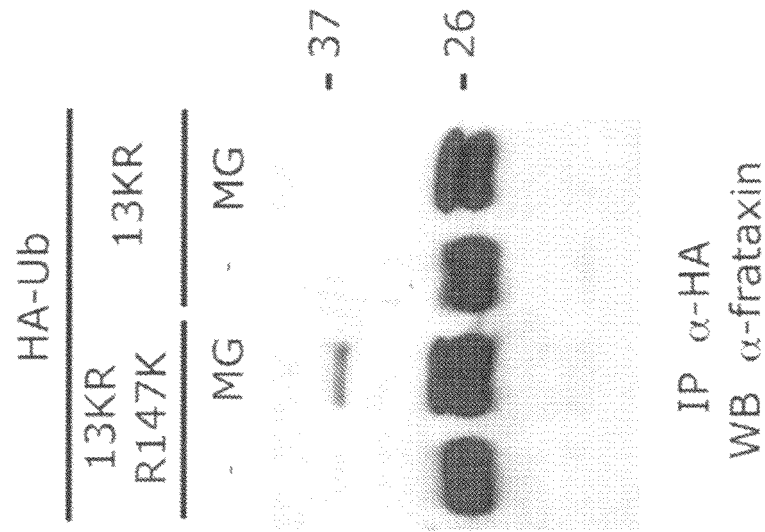
FIG. 3 illustrates that $K^{147}$ is the main ubiquitination target.
Figure 3:
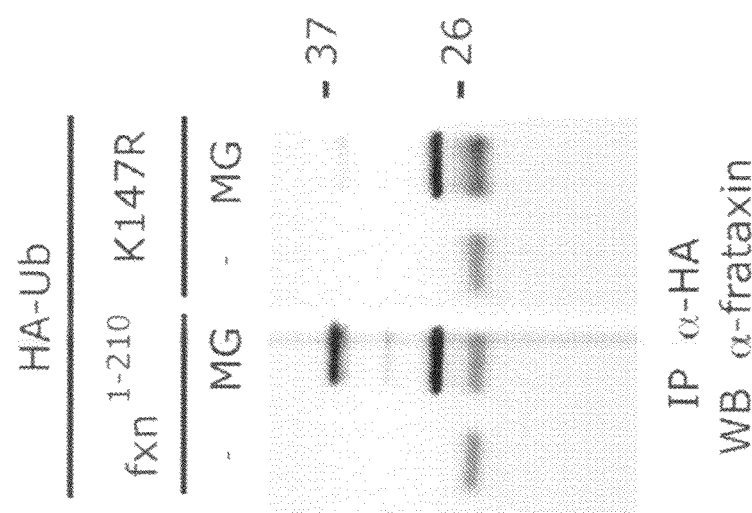
Figure 3:
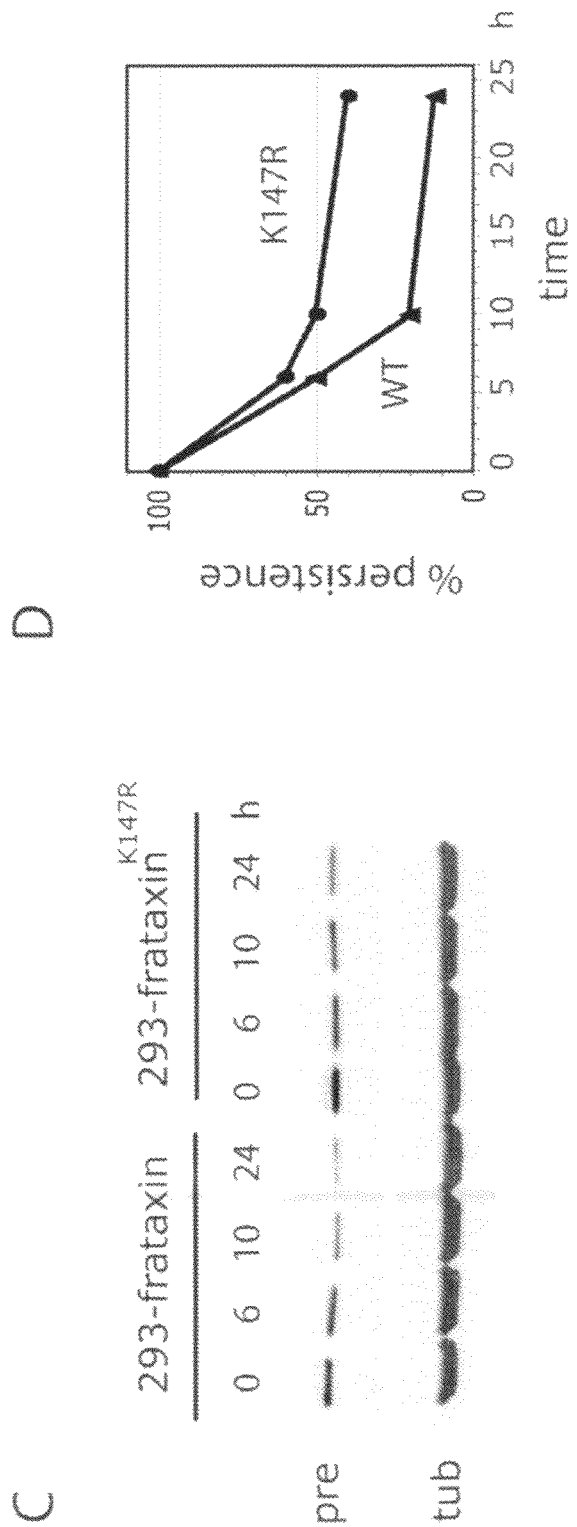

HEK-293 cells transiently transfected with HA-tagged ubiquitin (HA-Ub) and frataxin$^{1-210}$ or $K^{147}$-mutant frataxin (K147R) were treated with 10 μM MG132 (MG) for 16 h. Anti-HA immunoprecipitates were analyzed by WB with anti-frataxin antibody to detect ubiquitin-conjugated frataxin. One representative experiment out of five performed with similar results is shown in FIG. 3A.

HEK-293 cells transiently transfected with HA-Ub and the lysine-less frataxin mutant (13KR) or the lysine-less frataxin mutant in which $K^{147}$ has been reintroduced (13KR-R147K) were treated with 10 μM MG132 for 16 h. Anti-HA immunoprecipitates were analyzed as in A. One representative experiment out of two performed with similar results is shown in FIG. 3B.

HEK-293 Flp-In cells stably expressing frataxin$^{1-210}$ (HEK-293-frataxin) or the K147R frataxin mutant (HEK-293-frataxin$^{K147R}$) were treated for the indicated times with 100 μg/ml cycloheximide (CHX) to block new protein synthesis. Proteins were resolved on SDS-PAGE and revealed with anti-frataxin antibody or anti-tubulin, as a loading control. Pre: frataxin precursor. One representative experiment out of three performed with similar results is shown in FIG. 3C.

Densitometric analysis of frataxin precursor levels as shown in A normalized to tubulin levels. The graph in FIG. 3D shows the time-dependent decline upon CHX treatment.

Frataxin contains 13 lysines that represent possible ubiquitination targets. To map the critical lysine(s) we underwent a systematic site-specific mutagenesis of each and all frataxin lysines with arginines. The resulting frataxin mutants were transiently co-transfected with HA-Ub in HEK-293 cells exposed to MG132 to screen for the accumulation of ubiquitinated frataxin. This analysis allowed the identification of $K^{147}$ as the key target residue for frataxin ubiquitination. In fact, when the mutant frataxin$^{K147R}$ is transiently co-transfected with HA-Ub in HEK-293 cells exposed to MG132, the accumulation of mono-ubiquitinated frataxin cannot be detected (FIG. 3A). Moreover, while the knock-down of all the 13 lysines of frataxin (13KR) virtually abrogated any ubiquitination of frataxin, the reintroduction of $K^{147}$ in the lysine-less mutant was sufficient to restore the ubiquitination signal (FIG. 3B). Therefore $K^{147}$ is a major target of ubiquitination in frataxin and it is necessary for ubiquitination of the protein. Strikingly, among the 13 lysines of frataxin, $K^{147}$ is the most conserved across species (Table 1).

Frataxin$^{K147R}$ is Resistant to UPS-Mediated Degradation.

The loss of the ubiquitin docking site should grant the frataxin$^{K147R}$ mutant a relative resistance to UPS-mediated degradation, thus increasing its stability. To test this prediction, frataxin$^{K147R}$ was stably expressed in HEK-293 cells. After exposure to cycloheximide to block new protein synthesis, the stability of the frataxin$^{K147R}$ precursor was monitored over time and compared to the stability of frataxin precursor of HEK-293 cells stably expressing wild type frataxin$^{1-210}$ and similarly treated. FIG. 3C-D shows that the frataxin$^{K147R}$ precursor is significantly more stable (~45% of the input after 24 h) than the frataxin$^{1-210}$ precursor (~15% of the input after 24 h).

$K^{147}$ is Part of a Druggable Molecular Surface.

Figure 4:
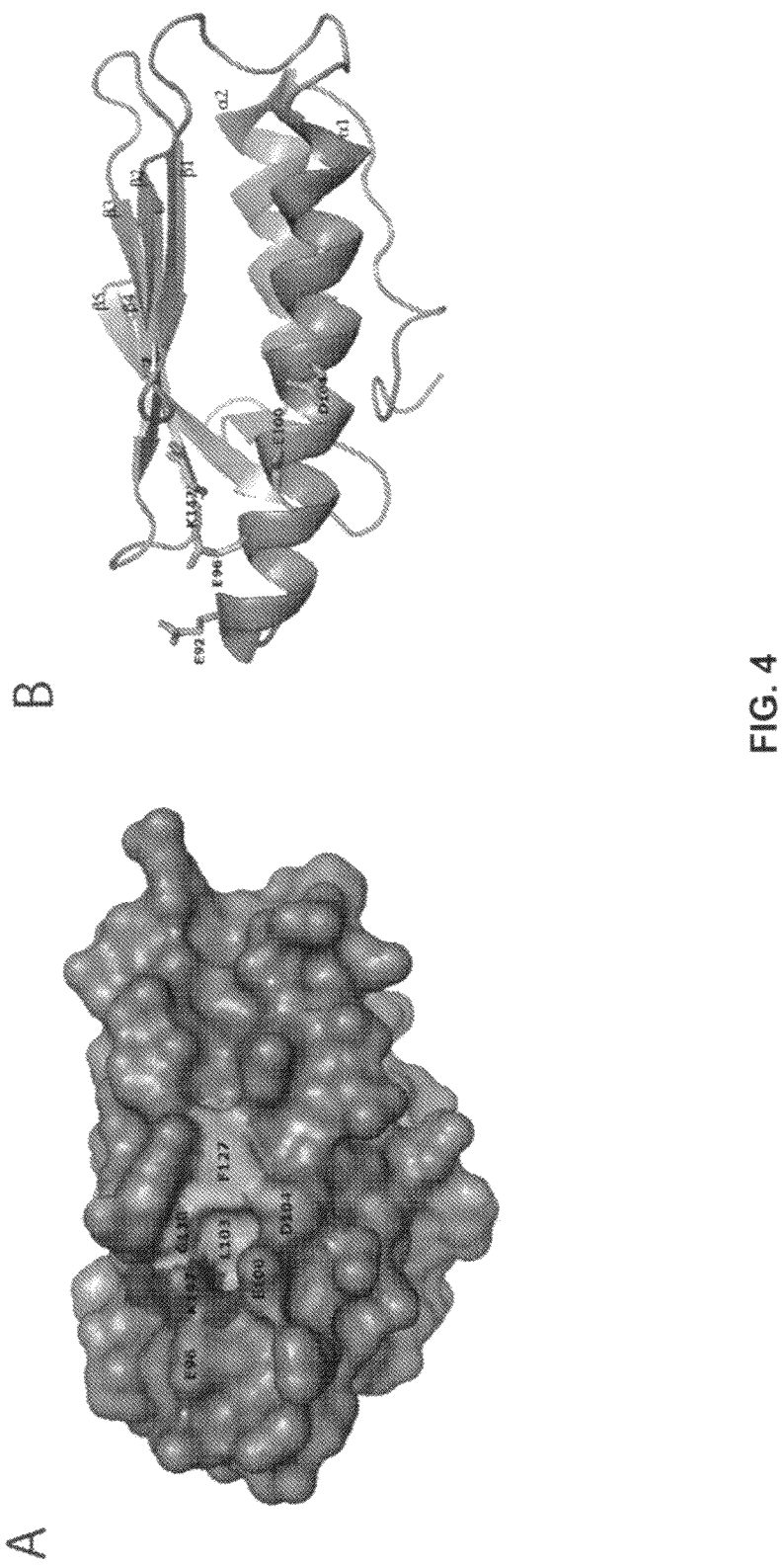
FIG. 4 illustrates that $K^{147}$ is part of a druggable molecular surface.
Figure 4:
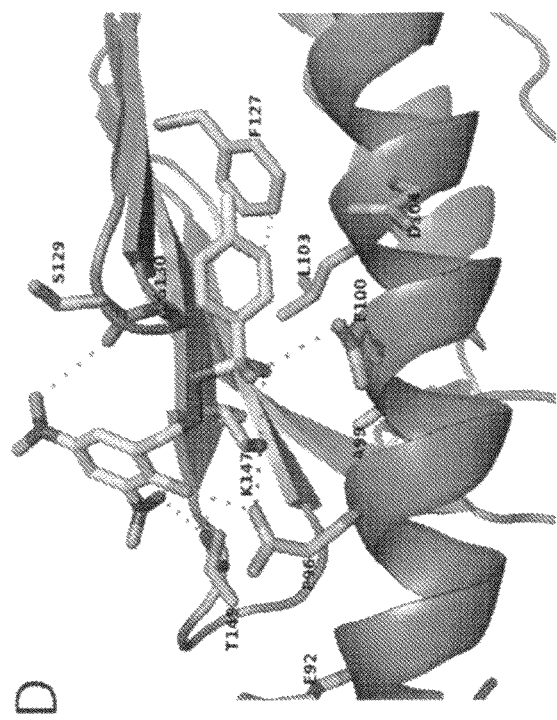
Figure 4:
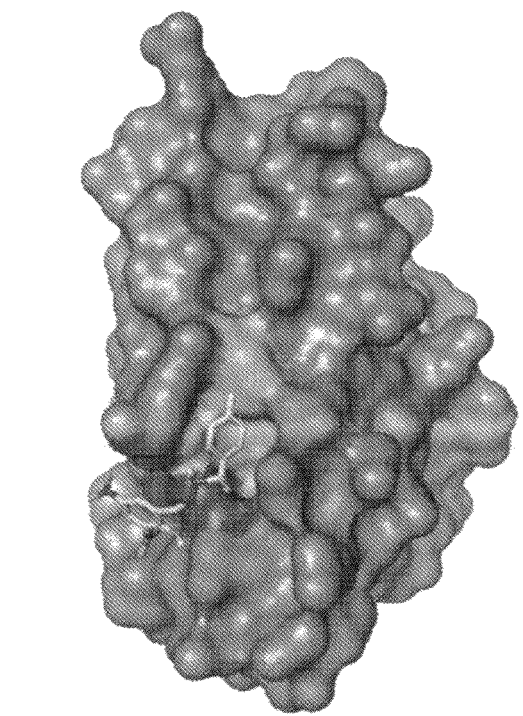

FIG. 4A illustrates solvent-accessible surface of frataxin. The binding site near $K^{147}$ includes $E^{96}$, $E^{100}$, $D^{104}$, $F^{127}$, $G^{130}$, $L^{103}$, and $A^{99}$. The latter aminoacid, omitted for clarity, is at the left of $L^{103}$ at the bottom of the cleft.

FIG. 4B is a cartoon representation of frataxin illustrating charged residues of the putative binding surface near $K_{147}$. $E^{96}$ is likely to form a stabilizing bond with $K^{147}$.

FIG. 4C illustrates the compound Formula III on the molecular surface of frataxin.

FIG. 4D illustrates selected interactions between frataxin and the ligand.

Ubiquitin-Competing Molecules Prevent Frataxin Ubiquitination.

Formula III prevents frataxin ubiquitination. HEK-293 cells were transiently co-transfected with HA-Ub and either frataxin$^{1-210}$ or lysine-mutant frataxin (K147R). Where indicated, cells were pretreated with 20 μM or 50 μM formula III one hour before transfection. The molecule was re-added 24 hours after transfection and cells were harvested 48 hours after transfection. Where indicated, cells were also treated with 10 μM MG132 for the last 16 hours. Total cell extracts (upper panel) or anti-HA immunoprecipitated proteins (lower panel) were detected with anti-frataxin antibody. One representative experiment out of three performed with similar results is shown in FIG. 5A.

Formula III induces frataxin precursor accumulation. HEK-293 Flp-In cells stably expressing frataxin$^{1-210}$ were treated for the indicated days with 20 μM of Formula III or 10 μM MG132. Total cell extracts were resolved on SDS-PAGE and analyzed with anti-frataxin antibody, or anti-tubulin, as a loading control. One representative experiment out of three performed with similar results is shown in FIG. 5B.

Formula III induces mature frataxin accumulation. HEK-293 Flp-In cells stably expressing frataxin$^{1-210}$ were treated and analyzed as in B. One representative experiment out of three performed with similar results is shown FIG. 5C.

Figure 5:
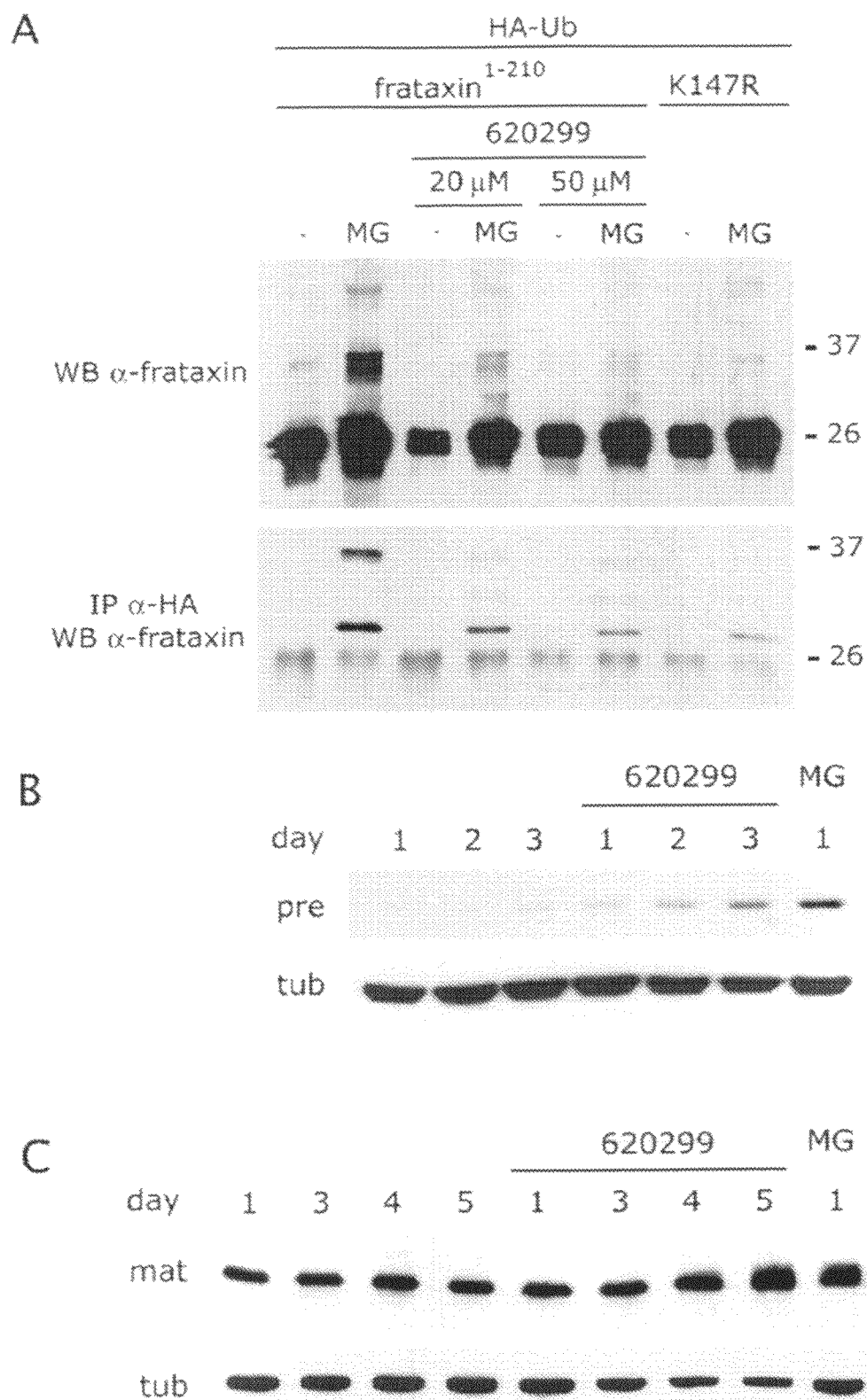
FIG. 5 illustrates that ubiquitin-competing molecules prevent frataxin ubiquitination.

To verify that putative ubiquitin-competing molecules were in fact able to interfere with the accessibility of $K^{147}$, thus preventing frataxin ubiquitination, HEK-293 cells were transiently co-transfected with HA-tagged ubiquitin (HA-Ub) and frataxin$^{1-210}$, in the presence of 20 μM and 50 μM of Formula III (FIG. 5A). Ubiquitinated frataxin was revealed after 48 h, by Western Blotting of total cell lysates (upper panel) and of anti-HA immunoprecipitates (lower panel). HEK-293 cells were also transiently co-transfected with HA-tagged ubiquitin (HA-Ub) and the frataxin$^{K147R}$ mutant (K147R) that lacks the ubiquitinable lysine, as a negative control. Collectively, FIG. 5A clearly shows that Formula III efficiently prevents the ubiquitination of frataxin$^{1-210}$ in a dose-dependent manner.

Preventing ubiquitination should result in a reduced degradation and consequent accumulation of frataxin. To test whether ubiquitin-competing molecules could induce the accumulation of frataxin, HEK-293 Flp-In cells stably expressing frataxin$^{1-210}$ were exposed to Formula III for the days indicated, and the accumulation of the frataxin precursor (FIG. 5B) and mature frataxin (FIG. 5C) was quantitated by WB. Thus the treatment of HEK-293 cells stably expressing frataxin with Formula III is able to induce substantial accumulation of both the frataxin precursor and, over a longer time period, of mature frataxin.

Ubiquitin-Competing Molecules are Effective in FRDA Cells.

FRDA lymphoblasts GM15850 were cultured for 6 days in the presence of 50 μM Formula IV or Formula VI. Cells were then fixed, stained with anti-frataxin antibody or anti-Bcl2, as a control, and analyzed by flow cytometry. One representative experiment out of three performed with similar results is shown as FIG. 6A.

FRDA lymphoblasts GM15850, GM16798 and GM16214 were left untreated or cultured for 6 days in the presence of 50 μM Formula IV. Their respective genetically-related healthy control GM15851, GM16241 and GM16215 lymphoblasts were left untreated and shown for comparison in FIG. 6B. Total cell extracts were resolved on SDS-PAGE and analyzed with anti-frataxin antibody, or anti-tubulin, as a loading control.

Figure 6:
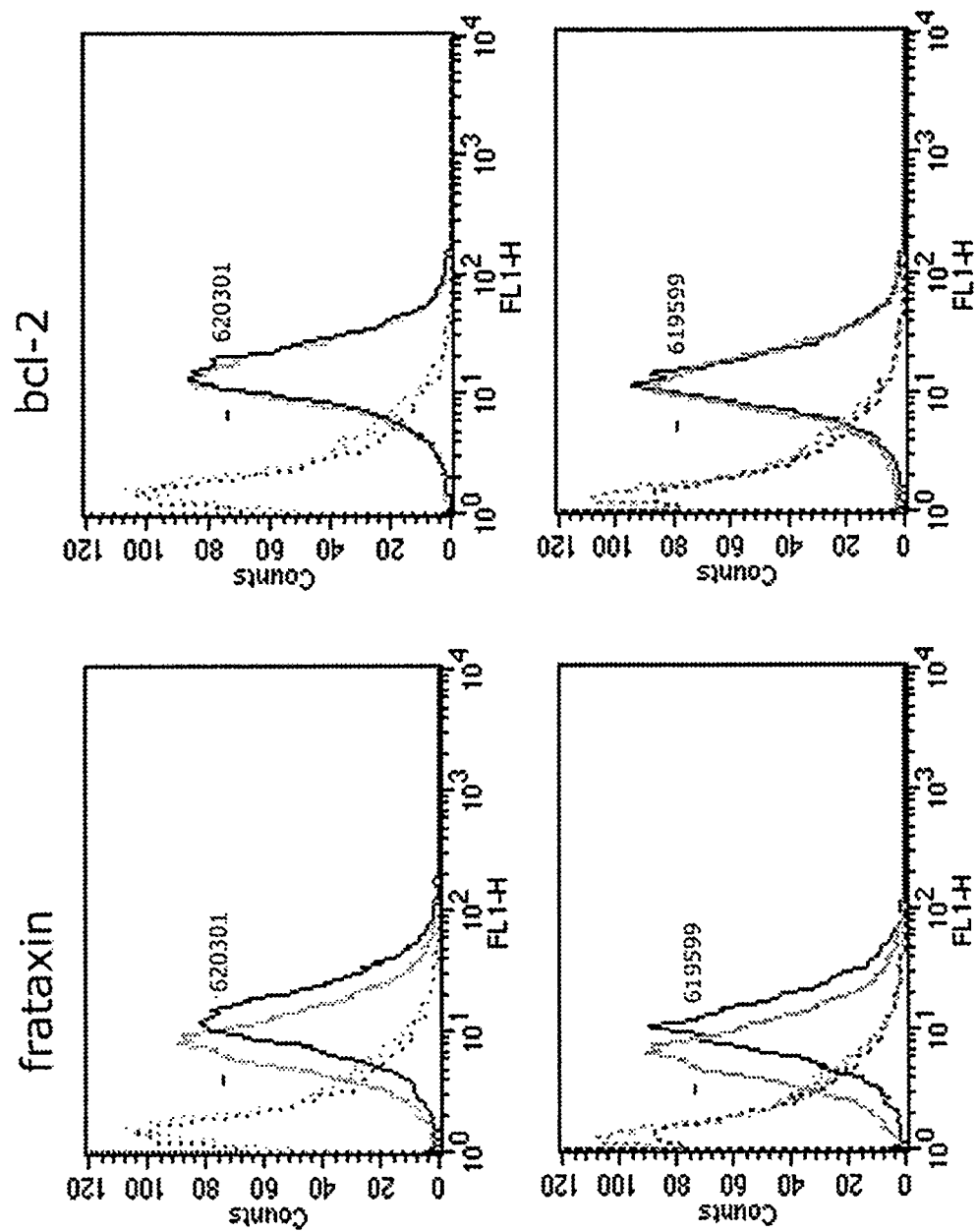
FIG. 6 illustrates that ubiquitin-competing molecules induce frataxin accumulation and rescue both aconitase and ATP defects in FRDA lymphoblasts.
Figure 6:
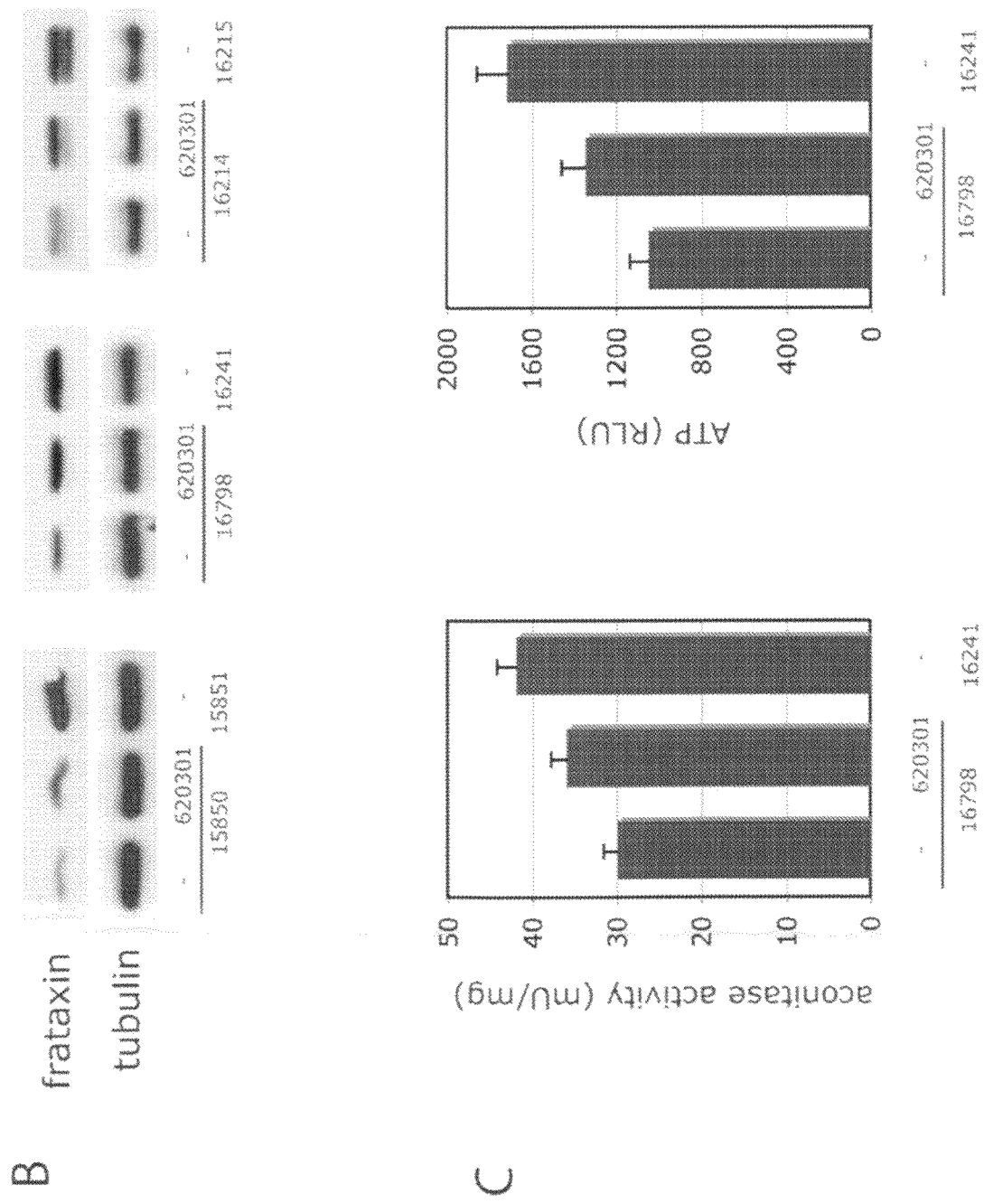

FRDA lymphoblasts GM16798 were left untreated or treated for 6 days with 50 μM Formula IV. Their genetically-related healthy control GM16241 lymphoblasts were left untreated. FIG. 6C shows the results. Aconitase activity and ATP levels were measured as described previously.

Among the different ubiquitin-competing molecules, compounds of Formula IV and Formula VI appeared to be best tolerated by FRDA cells. Lymphoblasts (GM15850 cells) derived from a FRDA patient were therefore exposed to these compounds for different time periods. As shown in FIG. 6A, FACS analysis reveals a discrete frataxin accumulation detectable in all cells after 6 days of treatment with both molecules. The accumulation of mature frataxin can be detected by SDS-PAGE and western blot analysis in GM15850 cells, as well as in lymphoblasts derived by two additional FRDA patients (GM16798 and GM16214 cells) exposed to Formula IV for 6 days. Frataxin levels in the respective genetically-related healthy control-derived cell lines are also shown for comparison.

Whether the increase in frataxin levels induced by exposure to ubiquitin-competing molecules would result in some functional rescue of FRDA cells was investigated. FIG. 6C shows that exposure of GM16798 lymphoblasts to Formula IV is able to significantly boost both aconitase activity and ATP levels after 6 days of treatment. Aconitase and ATP levels of the respective genetically-related healthy control-derived lymphoblasts are also shown for comparison.

Figure 7:
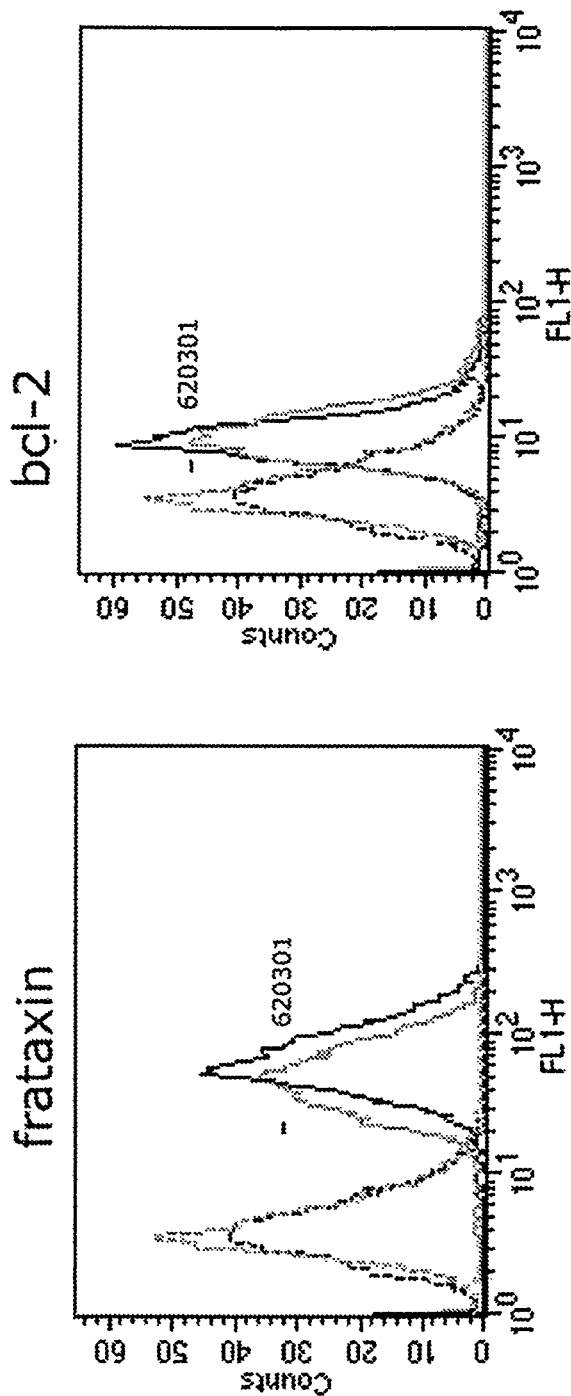
FIG. 7 illustrates that ubiquitin-competing molecules induce frataxin accumulation and rescue ATP defects in FRDA fibroblasts.
Figure 7:
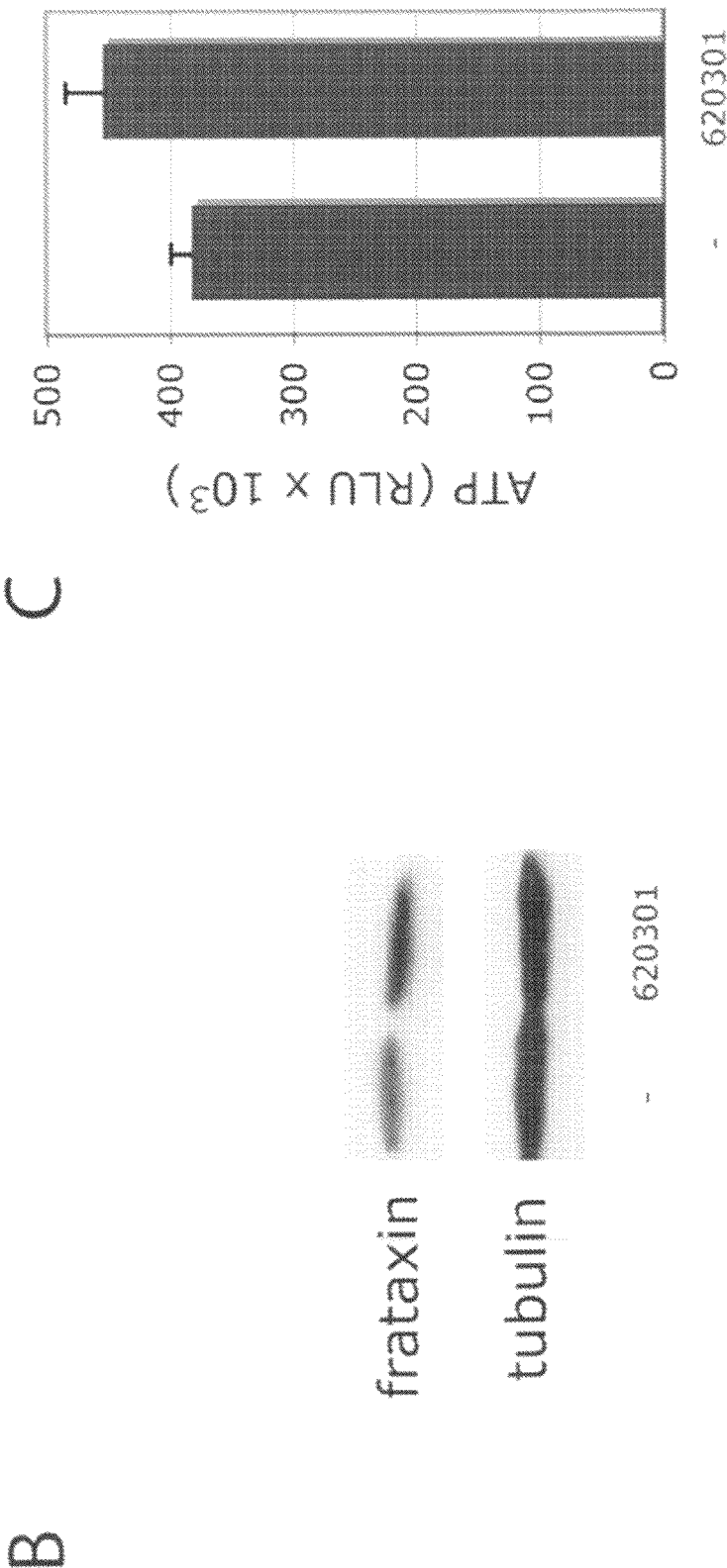

Similarly, FRDA fibroblasts (GM03816 cells) were exposed to compound Formula IV for different time periods FIG. 7 shows that frataxin accumulation can be detected as early as 3 days of treatment by both FACS analysis or SDS-PAGE and western blot analysis. Rescue of ATP levels can also be achieved in GM03816 fibroblasts exposed to Formula IV after 3 days of treatment (FIG. 7). FRDA fibroblasts GM03816 were treated for 3 days with 100 μM Formula IV. Cells were then fixed, stained with anti-frataxin antibody or anti-Bcl2, as a control, and analyzed by flow cytometry. One representative experiment out of three performed with similar results is shown in FIG. 7A. FRDA fibroblasts GM03816 were treated as above. Total cell extracts were resolved on SDS-PAGE and analyzed with anti-frataxin antibody, or anti-tubulin, as a loading control. FIG. 7B shows the results. FRDA fibroblasts GM03816 were treated as above. ATP levels were quantitated as described previously. Results are shown in FIG. 7C.

Figure 8:
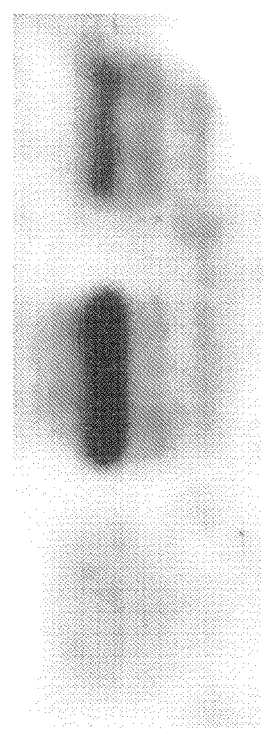
FIG. 8 illustrates that ubiquitin-competing molecules induce frataxin accumulation in HEK-293 cells.
Figure 8:
Figure 8:
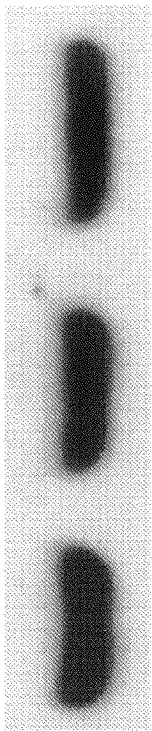
Figure 8:
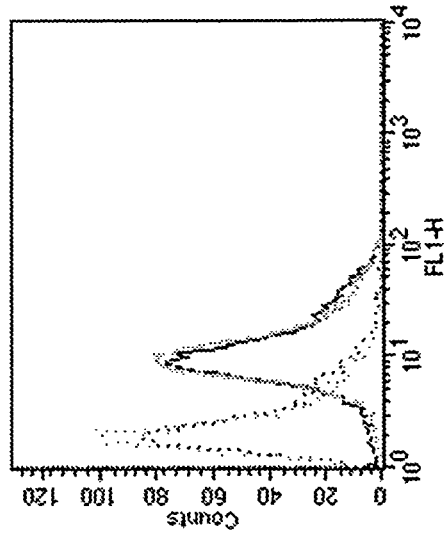
Figure 8:
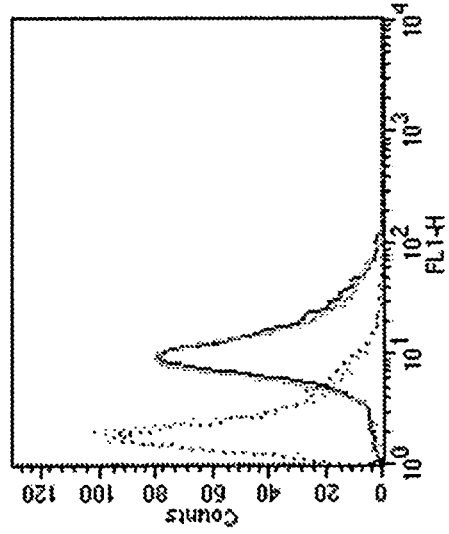
Figure 8:
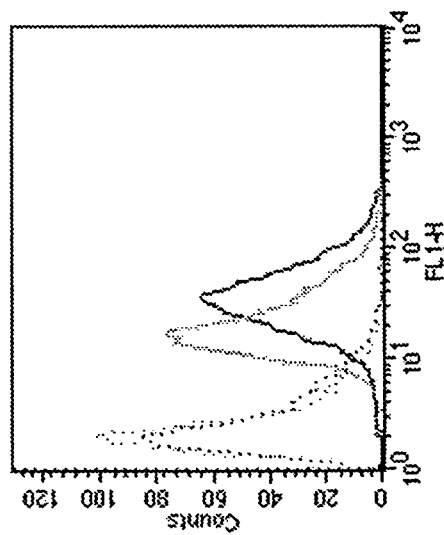
Figure 8:
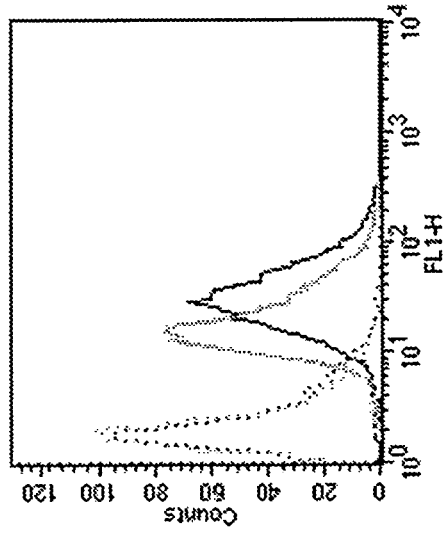

Compounds of Formulas IV and VI were also effective in inducing frataxin accumulation in HEK-293 Flp-In cells stably expressing frataxin$^{1-210}$ as quantitated by WB and FACS analysis (FIG. 8). 293 Flp-In cells stably expressing frataxin$^{1-210}$ were either left untreated or treated with 100 μM Formula IV or Formula VI for 18 hours. Total cell extracts were resolved on SDS-PAGE and analyzed with anti-frataxin antibody or anti-tubulin as a loading control (tub). Both precursor (pre) and mature frataxin (mat) are shown in FIG. 8A. 293 Flp-In cells stably expressing frataxin$^{1-210}$ were treated as for FIG. 8A and analyzed by flow cytometry after staining with anti-frataxin antibody or anti-Bcl2, as a control. One representative experiment out of three performed with similar results is shown in FIG. 8B.

Alinda IVK/1053144 and IVK/1070211 are effective in inducing mature frataxin accumulation in FRDA cells. FRDA lymphoblasts (GM15850) were treated for 3 days with 100 mM of IVK/1053144 or IVK/1070211 (Alinda codes). Total cell extracts from treated cells and from untreated cells (−) were resolved on SDS-PAGE and analyzed with anti-frataxin antibody, or anti-tubulin antibody. FIG. 9 shows the results.

Together these data indicate that the mature frataxin that accumulates during treatment with the ubiquitin-competing molecules is functional and able to partially revert the mitochondrial dysfunction in FRDA cells.

Efficacy Testing on FRDA Mice.

To test the compounds in FRDA mice, mice that express only the human FXN gene in which a GAA expansion has been inserted will be used. These mice therefore lack murine frataxin and produce low levels of human frataxin. They show a variety of neuropathological signs that mimic the human disease, thus are currently considered the animal model that more closely represents the human FRDA genetic defect. This will verify that compounds that elevate frataxin in FRDA cells in vitro are also able to elevate frataxin levels in tissues and alleviate the pathology and the clinical picture in the FRDA mice.

FRDA mice will be treated at the doses indicated by preliminary toxicity studies in normal mice, and different regiments will be investigated. At the appropriate times, different biochemical, behavioural and histopathological parameters will be investigated. Locomotor activity will be assessed by examining the unrestricted movement of mice. Coordination ability will be quantitated using an accelerating rotarod treadmill. Muscle strength will be measured by a forelimb grip test. Sections of the brain, spinal cord and dorsal root ganglia, liver and heart will be examined immunohistochemically to quantitate the amount of cellular frataxin and the reversal of iron accumulation and tissue degenerative changes. The activity of aconitases, as a measure of ISC-containing enzymatic function, will be also quantitated. An integrated efficacy score will be assigned to the tested compounds. A detailed pharmacokinetics/dynamics (ADME) analysis will eventually be started for those compounds which show the most promising activity.

The information that ubiquitination of frataxin on $K^{147}$ is crucial for its degradation, prompted investigation of the possibility of increasing frataxin levels by interfering with ubiquitination on $K^{147}$ by tailored drug design.

$K^{147}$, together with residues $E^{96}$, $E^{100}$, $D^{104}$, $F^{127}$, $G^{130}$, $L^{103}$, and $A^{99}$ surrounds a well defined cavity on the surface of frataxin (FIG. 4A-B). This cleft was chosen for in silico targeting in a virtual screening approach using the NCI chemical library.

The search for inhibitors of frataxin at the K147 site has been extended starting from the compound of Formula III, using an in-house database of conformers. The structure of Formula III has been subjected to conformational analysis and 16 conformers have been defined as representative of low-energy accessible conformational space for that molecule. These structures have been used to screen a database of ~500K lead-like molecules (~50M conformers), looking for similar structures (USR alghoritm, similarity >=0.85). 195 molecules were identified and docked on the structure of frataxin.

The area near $K^{147}$ of frataxin, as defined by the x-ray structure of the protein (PDB code: 1EKG) was used as target. This site includes E100, L103, D104, F127, G128, S129, G130, and $K^{147}$: The area near $K^{147}$ as defined by NMR models for frataxin (PDB code 1LY7) was also used. The available NMR structures (15 models) were analyzed with the same procedure used for the x-ray structure (program PASS). Three out of fifteen NMR models show a large pocket in the vicinity of $K^{147}$. One of these, model #7 in 1LY7, has been chosen for the docking studies, because it shows the largest pocket and because it is the most similar to the x-ray structure.

The virtual screening of the selected compounds has been carried out using the docking program Autodock/Vina. The docking region has been centered on the coordinates of the Cb of K147, with a grid of 16×16×16 Å with spacing of 0.375 Å. The docked structures were sorted by affinity for 1EKG and 1LY7, and 61 were selected for further analysis. Example selected compounds include:

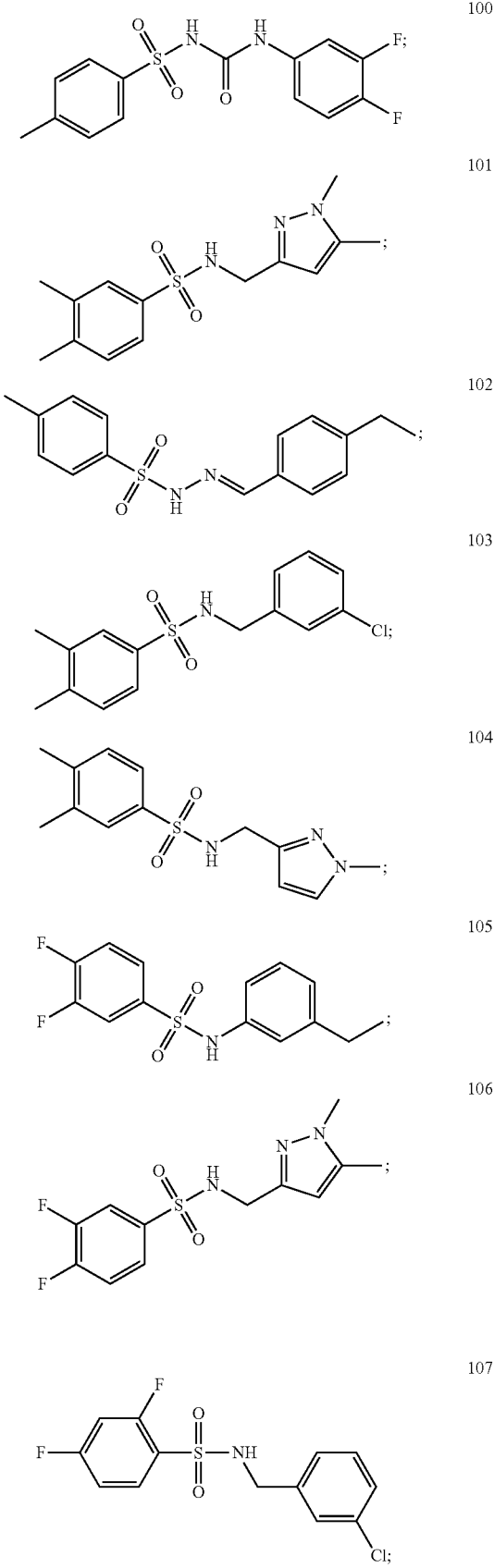

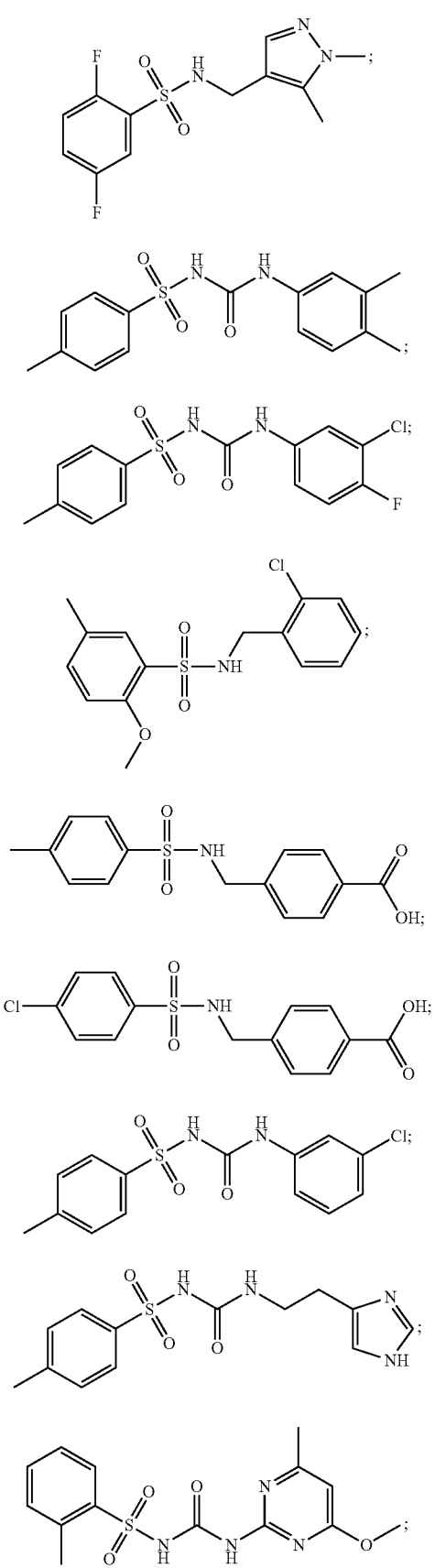
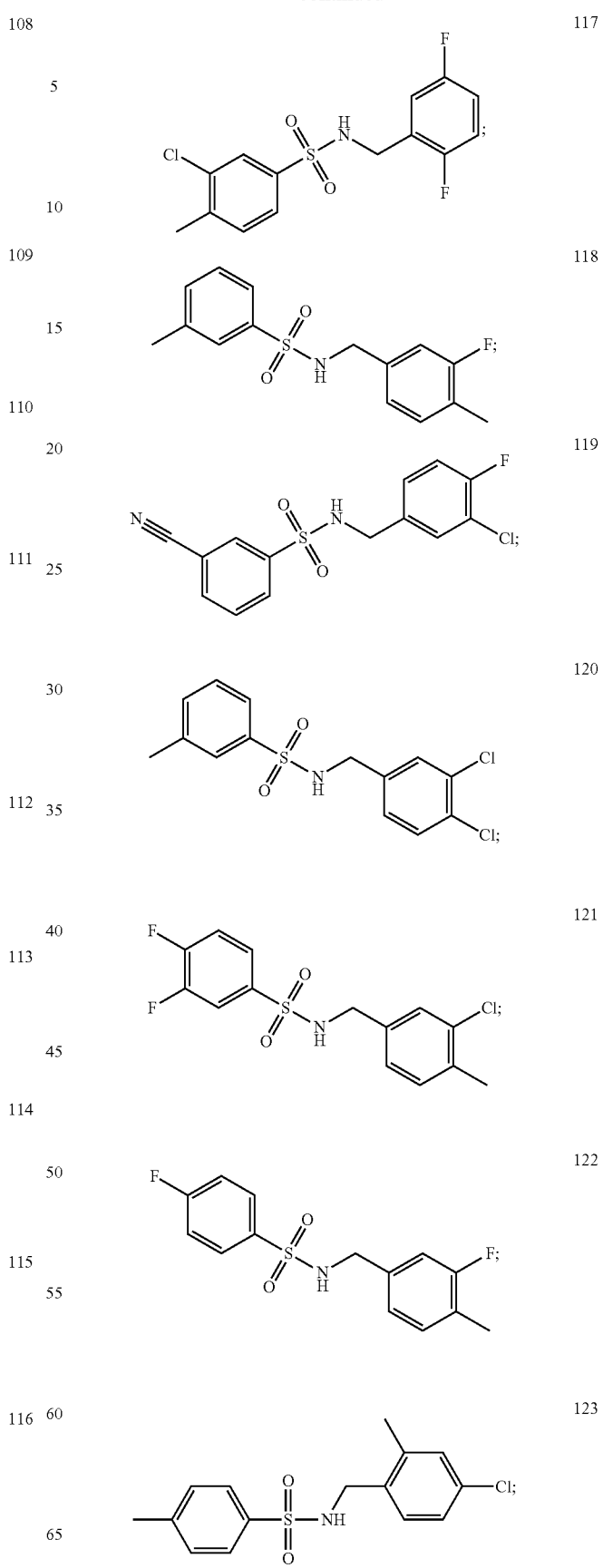

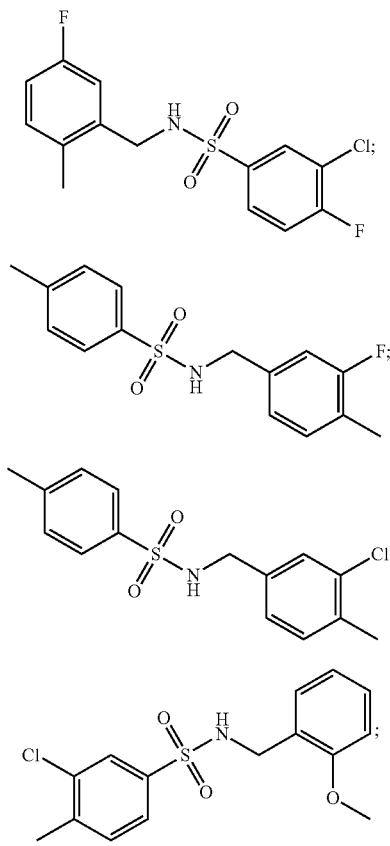
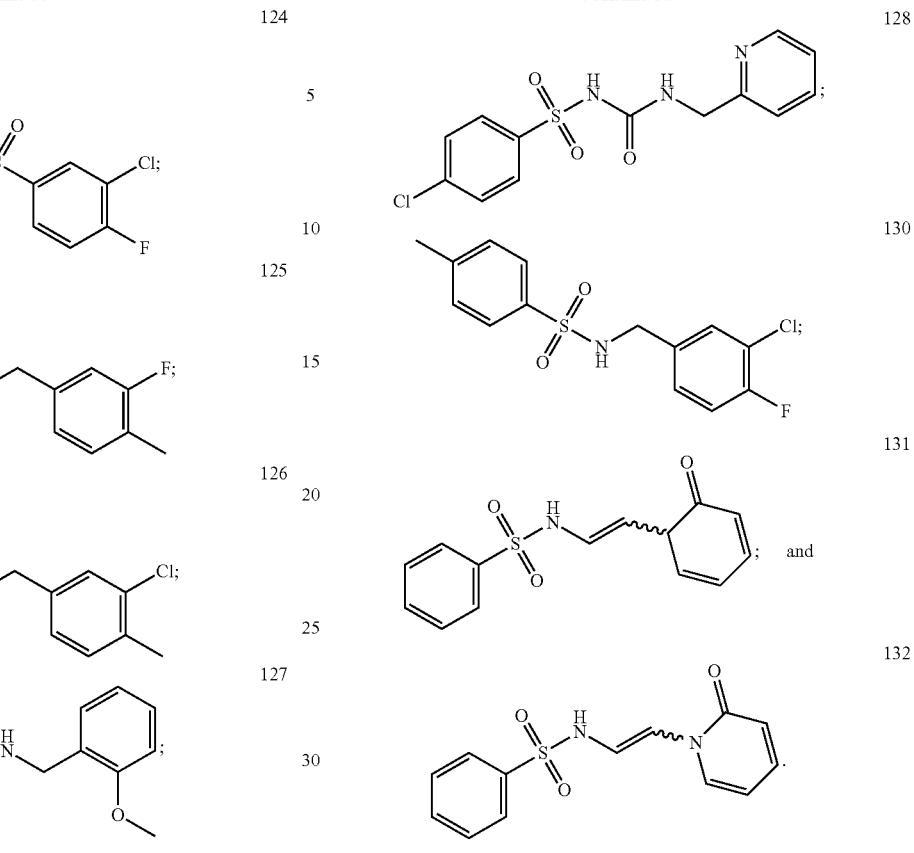

TABLE 1

Alignment of frataxin sequences from different species (SEQ ID NOS 1-16, respectively, in order of appearance). $K^{147}$ is in italics and other lysines are in bold. CLUSTAL 2.0.12 multiple sequence alignment

| | | |
|---|---|---|
| Homo-sapiens | ------MWTLGRRAVAGLLASPS-PAQAQTLTRVPRPAELAPLCGRRGLR | 43 |
| Macaca-fascicularis | ------MWTFGRRAVAGLLASPS-PAQAQTLTRAPRLAELAQLCSRRGLR | 43 |
| Bos-taurus | ------MWTLGRRSVASFLPRSALPGFAPTRAGAPRPAKDLSLSGLPGLR | 44 |
| Canis-familiaris | ------MWTLGRRAAAGLLPRSAPPGSAAAGAGTRGPTRAAPLHGGRGLR | 44 |
| Mus-musculus | ------MWAFGGRAAVGLLPRTA--SRASAWVGNPRWREPIVTCGRRGLH | 42 |
| Danio-rerio | -------MSSGLNSISG----------------GRSVSSANICGR---- | 22 |
| Drosophila-melanogaster | --------MFAGRLMVRSIVGRACLATMGRWSKPQAHASQVILPSTPAI- | 41 |
| Caenorhabditis-elegans | --------MLS----------------------------TILRNN---- | 9 |
| Saccharomyces-cerevisiae | ------------------MIKRSLASLVRVSSVMGRR-YMIAAAGGERA | 30 |
| Candida | ------------------MFKRFALNTAKALSKPAYS-QQLIYP---QV | 27 |
| Dictyostelium | --------------MIFNFLNKASNKTHTKLLLFSSIRNRILINNISSTS | 36 |
| Arabidopsis-thaliana | MA--------TASRFLLRKLPRFLKLS--PTLLRSNGVRVSSNLIQDSIE | 40 |
| Zea | MASRKLLVGLTARRQLQSRTQQLFWATSLPEATTSRSLMVAAAMARLSDR | 50 |
| Schizosaccharomyces-pombe | -----------------------------------------MQSLRAAFR | 9 |
| Cryptococcus-neoformans | -------------------------------------MLAAKNCLNKSLR | 13 |
| Trypanosoma | -------------------------------MRRTCCATTSAVLRSLVYL | 19 |

TABLE 1-continued

Alignment of frataxin sequences from different species (SEQ ID NOS 1-16, respectively, in order of appearance). K$^{147}$ is in italics and other lysines are in bold. CLUSTAL 2.0.12 multiple sequence alignment

| | | |
|---|---|---|
| Homo-sapiens | TDIDATCTPRRASSNQRGLNQIWNVKKQSVYLMNLRKSGTLGHPGSLDET | 93 |
| Macaca-fascicularis | TGINATRTTHHTSSNLRGLNQIRNVKRQSVYLMNLRKSGTLGHPGSLDDT | 93 |
| Bos-taurus | IGTAKAPARSQSSLSLRCLNQTLDVKKQSVCWINLRTAGTLGDAGTLDDT | 94 |
| Canis-familiaris | VGTGAARGPSHANLSLHHLNQLVNVKKQSVCLMNMRTVGTVSSPGSLDET | 94 |
| Mus-musculus | VTVNAG-ATRHAHLNLHYL-QILNIKKQSVCVVHLRNLGTLDNPSSLDET | 90 |
| Danio-rerio | --------------HTQCFDRILN--KRDLHLSGPLGEEKAHHLREISEA | 56 |
| Drosophila-melanogaster | -------------------AAVAIQCEEFTANRRLFSSQIETESTLDGA | 71 |
| Caenorhabditis-elegans | -------------------------------FVRRSFSSRIFSQN----- | 23 |
| Saccharomyces-cerevisiae | RFCPAVTNKKNHTVNTF-QKRFVESSTDGQVVPQEVLNLP--------LE | 71 |
| Candida | RFITQTLPTVACGLRPLGSVRTYSLSTEGEAIDDKIDKIT--------DN | 69 |
| Dictyostelium | KWSSINNNNKQSSVSKTNIFIITTHNKQQQQLSKSFSTINNNTKPISDVN | 86 |
| Arabidopsis-thaliana | PLDSFWRIGSRIRHDS---LTTRSFSSQGPASVDYSSVLQ--------EE | 79 |
| Zea | SSAPFILSSRAISSTQPVMQSTGDVSGSSPSAVDHKLAMQ--------ED | 92 |
| Schizosaccharomyces-pombe | RRTPIFLKPYEFSTNVFGLRCRYYSQVRHNGALT--------------DL | 45 |
| Cryptococcus-neoformans | ALRPLTERSASPVIARSARASPLLRSRATSARTPPTSTLS--------HD | 55 |
| Trypanosoma | RPHGRAKPTTSGSGRKERQFSTTTARCESKGWHPAKLGMDG-----FTDV | 64 |
| Homo-sapiens | TYERLAEETLDSLAEFFEDLADKPYTFEDYDVSFGSGVLTVKLGGDLGTY | 143 |
| Macaca-fascicularis | TYERLAEETLDSLAEFFEDLADKPYTFEDYDVSFGSGVLTVKLGGDLGTY | 143 |
| Bos-taurus | TYERLAEETLDSLAEFFEDLADKPYTFEDYDVSFGSGVLTVKLGGDLGTY | 144 |
| Canis-familiaris | TYERLAETTLDSLAEFFEDLADKPYTLEDYDVSFGSGVLTVKLGGDLGTY | 144 |
| Mus-musculus | AYERLAEETLDSLAEFFEDLADKPYTLEDYDVSFGDGVLTIKLGGDLGTY | 140 |
| Danio-rerio | EYERLAEETLDALADYFEDLTDENFTGLDYDVVFSNGVLTVKVGSDHGTY | 106 |
| Drosophila-melanogaster | TYERVCSDTLDALCDYFEELTENASELQGTDVAYSDGVLTVNLGGQHGTY | 121 |
| Caenorhabditis-elegans | EYETAADSTLERLSDYFDQIADSFPVSEQFDVSHAMGVLTVNVSKSVGTY | 73 |
| Saccharomyces-cerevisiae | KYHEEADDYLDHLLDSLEELSEA-HPDCIPDVELSHGVMTLEIP-AFGTY | 119 |
| Candida | EYAKVSNEYLENLSDSLEELNED-FEQ--VDSELSQGVLTLTLP-PNGTY | 115 |
| Dictyostelium | LFHDIVDEEFELFVDRLEILSEA-NTCEGFEVEGNDGVLTIIVG-NKGTY | 134 |
| Arabidopsis-thaliana | EFHKLANFTINHLLEKIEDYGDN-VQIDGFDIDYGNEVLTLKLG-SLGTY | 127 |
| Zea | EFHKLADETIHDLLEKLEEYGDS-IQMDGFDIEYGNQVLTLRLG-DLGTY | 140 |
| Schizosaccharomyces-pombe | EYHRVADDTLDVLNDTFEDLLEE-VGKKDYDIQYANGVITLMLG-EKGTY | 93 |
| Cryptococcus-neoformans | EYEHVSERDMETLNESLEIFCED-FGNGNWEIEYSSGVLNLTLP-PYGTY | 103 |
| Trypanosoma | AYNTAADTFLERVESALETIGDT---DTLEDVNLAGGVLVIETT-SRGTF | 110 |
| |            :   .   :. . . :        :           *: :      **: | |
| Homo-sapiens | VIN*K*QTPNKQIWLSSPSSGPKRYDWTG----KNWVYSH-DGVSLHELLAA | 188 |
| Macaca-fascicularis | VIN*K*QTPNKQIWLSSPSSGPKRYDRTG----KNWVYSH-DGVSLHELLGA | 188 |
| Bos-taurus | VIN*K*QTPNKQIWLSSPSSGPKRYDWTG----RNWVYSH-DGVSLHELLAT | 189 |
| Canis-familiaris | VIN*K*QTPNKQIWLSSPSSGPKRYDWTG----KNWVYSH-DGVSLHELLAT | 189 |
| Mus-musculus | VIN*K*QTPNKQIWLSSPSSGPKRYDWTG----KNWVYSH-DGVSLHELLAR | 185 |
| Danio-rerio | VIN*K*QTPNRQIWLSSPTSGPKRYDWTG----ERWVYTH-DAVPLHSLLSK | 151 |

TABLE 1-continued

Alignment of frataxin sequences from different species (SEQ ID NOS 1-16, respectively, in order of appearance). $K^{147}$ is in italics and other lysines are in bold. CLUSTAL 2.0.12 multiple sequence alignment

| | | |
|---|---|---|
| Drosophila-melanogaster | VINRQTPNKQIWLSSPTSGPKRYDFVGTVAAGRWIYKH-SGQSLHELLQQ | 170 |
| Caenorhabditis-elegans | VINKQSPNKQIWLSSPMSGPKRYDLE---EEGKWTYAH-DGEQLDSLLNR | 119 |
| Saccharomyces-cerevisiae | VINKQPPNKQIWLASPLSGPNR--FDLLN--GEWVSLR-NGTKLTDILTE | 164 |
| Candida | VINKOPPNKQIWLSSPISGPKR--YDLIG--GKWVTLR-DGSSLTSLLQE | 160 |
| Dictyostelium | VINKQTPNRQIWWSSPLSGPKRFDYDSVE--KRWVDNR-DGTPLRQLLNS | 181 |
| Arabidopsis-thaliana | VLNKQTPNRQIWMSSPVSGPSRFDWDRDA--NAWIYRR-TEAKLHKLLEE | 174 |
| Zea | VINKQTPNKQIWLSSPVSGPSRFDWDATA--NGWIYKR-TGVNLVRLLEK | 187 |
| Schizosaccharomyces-pombe | VINKQPPAHQIWLSSPVSGPKHYEYSLKS--KTWCSTR-DEGTLLGILSS | 140 |
| Cryptococcus-neoformans | VLNKQPPNLQIWMSSPVSGPSRFEYIN----GSWVHHRKEGVKLGELLSG | 149 |
| Trypanosoma | VLNKQAPNVQLWLSSPLSGPHHYDMTTSATGSVEWRADADGHSLEERLEK | 160 |
| | *:*:*.*  *:*.:** ***  :                   *   * | |
| Homo-sapiens | ELTKALKTK-LDLSSLAYSGKDA------ | 210 |
| Macaca-fascicularis | ELTKALKTK-LDLSSLAYSGKDA------ | 210 |
| Bos-taurus | ELTQALKTK-LDLSALAYSGKDTCCPAQC | 217 |
| Canis-familiaris | ELTKAFKIK-LDLSSLAYSGKGT------ | 211 |
| Mus-musculus | ELTKALNTK-LDLSSLAYSGKGT------ | 207 |
| Danio-rerio | ELSIIFKTN-IDLSHLIHS---------- | 169 |
| Drosophila-melanogaster | EIPGILKSQSVDFLRLPYCS--------- | 190 |
| Caenorhabditis-elegans | EFRKILADDRIDFSRHV------------ | 136 |
| Saccharomyces-cerevisiae | EVEKAISKS-Q----------------- | 174 |
| Candida | EISSAIGQE-FTFENVEQ----------- | 177 |
| Dictyostelium | EINTLCKYD-MEI--------------- | 193 |
| Arabidopsis-thaliana | ELENLCGEP-IQLS-------------- | 187 |
| Zea | EIGELCGTP-VEL--------------- | 199 |
| Schizosaccharomyces-pombe | EFSKWFSRP-IEFKKSEDF---------- | 158 |
| Cryptococcus-neoformans | ELKEILEKSGNEAAAGVWDGVGLP----- | 173 |
| Trypanosoma | ELSDVVGTEVSLSSGAGETE--------- | 180 |

INFORMAL SEQUENCE LISTING

SEQ ID NO: 1

```
         10         20         30         40         50         60
MWTLGRRAVA GLLASPSPAQ AQTLTRVPRP AELAPLCGRR GLRTDIDATC TPRRASSNQR 70         80         90        100        110        120
GLNQIWNVKK QSVYLMNLRK SGTLGHPGSL DETTYERLAE ETLDSLAEFF EDLADKPYTF 130        140        150        160        170        180
EDYDVSFGSG VLTVKLGGDL GTYVINKQTP NKQIWLSSPS SGPKRYDWTG KNWVYSHDGV 190        200        210
SLHELLAAEL TKALKTKLDL SSLAYSGKDA
```

REFERENCES

The following references are hereby incorporated herein by reference in their entirety.

1. Pandolfo, M. & Pastore, A. The pathogenesis of Friedreich ataxia and the structure and function of frataxin. *J Neurol* 256 Suppl 1, 9-17 (2009).
2. Pandolfo, M. Friedreich ataxia: the clinical picture. *J Neurol* 256 Suppl 1, 3-8 (2009).
3. Puccio, H. Multicellular models of Friedreich ataxia. *J Neurol* 256 Suppl 1, 18-24 (2009).
4. Condo, I., et al. In vivo maturation of human frataxin. *Hum Mol Genet.* 16, 1534-1540 (2007).
5. Schmucker, S., Argentini, M., Carelle-Calmels, N., Martelli, A. & Puccio, H. The in vivo mitochondrial two-step maturation of human frataxin. *Hum Mol Genet.* 17, 3521-3531 (2008).
6. Acquaviva, F., et al. Extra-mitochondrial localisation of frataxin and its association with IscU1 during enterocyte-like differentiation of the human colon adenocarcinoma cell line Caco-2. *J Cell Sci* 118, 3917-3924 (2005).
7. Condo, I., Ventura, N., Malisan, F., Tomassini, B. & Testi, R. A pool of extramitochondrial frataxin that promotes cell survival. *J Biol Chem* 281, 16750-16756 (2006).
8. Condó, I., et al. Molecular control of the cytosolic aconitase/IRP1 switch by extramitochondrial frataxin. *Hum Mol Genet* doi:10.1093/hmg/ddp592 (2010).
9. Yoon, T. & Cowan, J. A. Iron-sulfur cluster biosynthesis. Characterization of frataxin as an iron donor for assembly of [2Fe-2S] clusters in ISU-type proteins. *J Am Chem Soc* 125, 6078-6084 (2003).
10. Bulteau, A. L., et al. Frataxin acts as an iron chaperone protein to modulate mitochondrial aconitase activity. *Science* 305, 242-245 (2004).
11. Adinolfi, S., et al. Bacterial frataxin CyaY is the gatekeeper of iron-sulfur cluster formation catalyzed by IscS. *Nat Struct Mol Biol* 16, 390-396 (2009).
12. Delatycki, M. B. Evaluating the progression of Friedreich ataxia and its treatment. *J Neurol* 256 Suppl 1, 36-41 (2009).
13. Schulz, J. B., Di Prospero, N. A. & Fischbeck, K. Clinical experience with high-dose idebenone in Friedreich ataxia. *J Neurol* 256 Suppl 1, 42-45 (2009).
14. Tsou, A. Y., Friedman, L. S., Wilson, R. B. & Lynch, D. R. Pharmacotherapy for Friedreich ataxia. *CNS Drugs* 23, 213-223 (2009).
15. Gottesfeld, J. M. Small molecules affecting transcription in Friedreich ataxia. *Pharmacol Ther* 116, 236-248 (2007).
16. Marmolino, D. & Acquaviva, F. Friedreich's Ataxia: from the (GAA)n repeat mediated silencing to new promising molecules for therapy. *Cerebellum* 8, 245-259 (2009).
17. Schwartz, A. L. & Ciechanover, A. Targeting proteins for destruction by the ubiquitin system: implications for human pathobiology. *Annu Rev Pharmacol Toxicol* 49, 73-96 (2009).
18. Treier, M., Staszewski, L. M. & Bohmann, D. Ubiquitin-dependent c-Jun degradation in vivo is mediated by the delta domain. *Cell* 78, 787-798 (1994).
19. Musco, G., et al. Towards a structural understanding of Friedreich's ataxia: the solution structure of frataxin. *Structure* 8, 695-707 (2000).
20. Dhe-Paganon, S., Shigeta, R., Chi, Y. I., Ristow, M. & Shoelson, S. E. Crystal structure of human frataxin. *J Biol Chem* 275, 30753-30756 (2000).
21. Brady, G. P., Jr. & Stouten, P. F. Fast prediction and visualization of protein binding pockets with PASS. *J Comput Aided Mol Des* 14, 383-401 (2000).
22. Trott, O. & Olson, A. J. AutoDock Vina: improving the speed and accuracy of docking with a new scoring function, efficient optimization, and multithreading. *J Comput Chem* 31, 455-461 (2010).
23. Irwin, J. J. & Shoichet, B. K. ZINC— a free database of commercially available compounds for virtual screening. *J Chem Inf Model* 45, 177-182 (2005).
24. Teague, S. J., Davis, A. M., Leeson, P. D. & Oprea, T. The Design of Leadlike Combinatorial Libraries. *Angew Chem Mt Ed Engl* 38, 3743-3748 (1999).
25. Deshaies, R. J. & Joazeiro, C. A. RING domain E3 ubiquitin ligases. *Annu Rev Biochem* 78, 399-434 (2009).
26. Rotin, D. & Kumar, S. Physiological functions of the HECT family of ubiquitin ligases. *Nat Rev Mol Cell Biol* 10, 398-409 (2009).
27. Xu, P., et al. Quantitative proteomics reveals the function of unconventional ubiquitin chains in proteasomal degradation. *Cell* 137, 133-145 (2009).
28. Boutet, S. C., Disatnik, M. H., Chan, L. S., Iori, K. & Rando, T. A. Regulation of Pax3 by proteasomal degradation of monoubiquitinated protein in skeletal muscle progenitors. *Cell* 130, 349-362 (2007).
29. Kravtsova-Ivantsiv, Y., Cohen, S. & Ciechanover, A. Modification by single ubiquitin moieties rather than polyubiquitination is sufficient for proteasomal processing of the p105 NF-kappaB precursor. *Mol Cell* 33, 496-504 (2009).
30. Saeki, Y., et al. Lysine 63-linked polyubiquitin chain may serve as a targeting signal for the 26S proteasome. *EMBO J* 28, 359-371 (2009).
31. Iwai, K. & Tokunaga, F. Linear polyubiquitination: a new regulator of NF-kappaB activation. *EMBO Rep* 10, 706-713 (2009).
32. Komander, D. The emerging complexity of protein ubiquitination. *Biochem Soc Trans* 37, 937-953 (2009).
33. Yonashiro, R., et al. A novel mitochondrial ubiquitin ligase plays a critical role in mitochondrial dynamics. *EMBO J* 25, 3618-3626 (2006).
34. Li, W., et al. Genome-wide and functional annotation of human E3 ubiquitin ligases identifies MULAN, a mitochondrial E3 that regulates the organelle's dynamics and signaling. *PLoS One* 3, e1487 (2008).
35. Germain, D. Ubiquitin-dependent and -independent mitochondrial protein quality controls: implications in ageing and neurodegenerative diseases. *Mol Microbiol* 70, 1334-1341 (2008).
36. Wright, G., Terada, K., Yano, M., Sergeev, I. & Mori, M. Oxidative stress inhibits the mitochondrial import of preproteins and leads to their degradation. *Exp Cell Res* 263, 107-117 (2001).
37. Habelhah, H., et al. Regulation of 2-oxoglutarate (alpha-ketoglutarate) dehydrogenase stability by the RING finger ubiquitin ligase Siah. *J Biol Chem* 279, 53782-53788 (2004).

The invention claimed is:

1. A method of treating Friedreich's Ataxia in a subject in need thereof, comprising administering to a subject a therapeutically effective amount of a compound of formula (I) or a pharmaceutically acceptable salt, tautomer, or stereoisomer thereof:

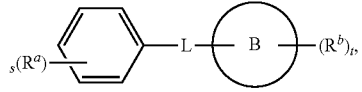

wherein:
- L is a linking group selected from the group consisting of —S(O)$_2$—NH—(CR$_2$)$_x$—, —S(O)$_2$—NH—N=, —S(O)$_2$—NH—N=(CR)— and —S(O)$_2$—NH—C(O)—NH—(CR$_2$)$_y$— wherein:
  - R is H or C$_1$-C$_4$ alkyl, and
  - x and y are each independently 0, 1 or 2;
- B is a 5- or 6-membered aromatic ring having 1 or 2 optional nitrogen heteroatoms;
- each R$^a$ and each R$^b$ are independently C$_1$-C$_6$ alkyl, C$_2$-C$_6$ alkenyl, C$_2$-C$_6$ alkynyl, C$_1$-C$_6$ alkoxy, oxo, halo, —NO$_2$, —CF$_3$, —CN, —OR$_9$, —SR$_9$, —C(O)R$_9$, —NHC(O)R$_9$, —C(O)OR$_9$, —OC(O)R$_9$, —NR$_{10}$R$_{11}$, —C(O)NR$_{10}$R$_{11}$, —NHR$_9$C(O)NR$_{10}$R$_{11}$, or —SO$_2$NR$_{10}$R$_{11}$, aryl, arylalkyl, cycloalkyl, or heterocycle, wherein:
  - R$_9$, R$_{10}$, and R$_{11}$ are independently H, C$_1$-C$_6$ alkyl, C$_2$-C$_6$ alkenyl, C$_2$-C$_6$ alkynyl, C$_1$-C$_6$ alkoxy, halo, aryl, arylalkyl, cycloalkyl, or heterocycle, each being optionally substituted with one to four substituents, and
  - two R$^a$ or two R$^b$ together with the atoms to which they attach on the ring optionally form a ring;
- s is 0, 1, 2 or 3; and
- t is 1, 2, 3 or 4.

2. The method of claim 1 wherein each R$^a$ is independently C$_1$-C$_6$ alkyl, halo, —NO$_2$, —CF$_3$, —CN, or —OR$_9$.

3. The method of claim 1 wherein each R$^b$ is independently C$_1$-C$_6$ alkyl, halo, —NO$_2$, —CF$_3$, —CN, or —OR$_9$.

4. The method of claim 1 wherein L is —S(O)$_2$—NH—N=(CH)— and one of the two carbons on ring A ortho to the attachment to L is unsubstituted.

5. The method of claim 1 wherein B is selected from the group consisting of a phenyl group, an imidazole, a pyridine and a pyrimidine.

6. The method of claim 1 wherein the compound has formula Ia:

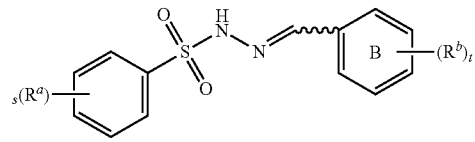

and t is 1, 2 or 3.

7. The method of claim 1 wherein the carbon on ring B para to the attachment point is unsubstituted.

8. The method of claim 1 wherein the compound has formula Ic:

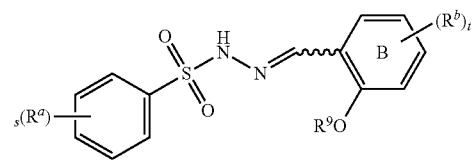

wherein t is 1, 2 or 3.

9. The method of claim 1 wherein at least one R$^b$ is —NO$_2$.

10. The method of claim 6 wherein t is 2 or 3 and at least one R$^b$ is a halogen.

11. The method of claim 1 wherein s is 1, 2 or 3 and at least one R$^a$ is a halogen.

12. The method of claim 1 wherein the compound has formula XII:

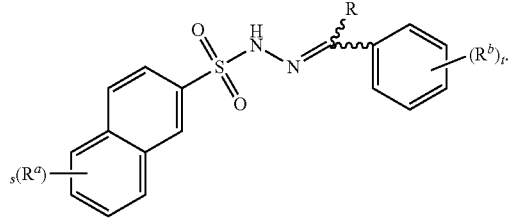

13. The method of claim 12 wherein s is 0.

14. The method of claim 1 wherein the method of treating Friedreich's Ataxia comprises inhibiting ubiquitination of frataxin in the subject.

15. The method claim 1 wherein the method of treating Friedreich's Ataxia comprises elevating intracellar frataxin levels in the subject.

16. The method of claim 1 wherein the subject is a mammal.

17. The method of claim 16 wherein the mammal is a human.

* * * * *

SEQUENCE LISTING

<160> NUMBER OF SEQ ID NOS: 16

<210> SEQ ID NO 1
<211> LENGTH: 210
<212> TYPE: PRT
<213> ORGANISM: Homo sapiens

<400> SEQUENCE: 1

Met Trp Thr Leu Gly Arg Arg Ala Val Ala Gly Leu Leu Ala Ser Pro
1               5                   10                  15

Ser Pro Ala Gln Ala Gln Thr Leu Thr Arg Val Pro Arg Pro Ala Glu
            20                  25                  30

Leu Ala Pro Leu Cys Gly Arg Arg Gly Leu Arg Thr Asp Ile Asp Ala
            35                  40                  45

Thr Cys Thr Pro Arg Arg Ala Ser Ser Asn Gln Arg Gly Leu Asn Gln
        50                  55                  60

Ile Trp Asn Val Lys Lys Gln Ser Val Tyr Leu Met Asn Leu Arg Lys
65                  70                  75                  80

Ser Gly Thr Leu Gly His Pro Gly Ser Leu Asp Glu Thr Thr Tyr Glu
                85                  90                  95

Arg Leu Ala Glu Glu Thr Leu Asp Ser Leu Ala Glu Phe Phe Glu Asp
            100                 105                 110

Leu Ala Asp Lys Pro Tyr Thr Phe Glu Asp Tyr Asp Val Ser Phe Gly
            115                 120                 125

Ser Gly Val Leu Thr Val Lys Leu Gly Gly Asp Leu Gly Thr Tyr Val
        130                 135                 140

Ile Asn Lys Gln Thr Pro Asn Lys Gln Ile Trp Leu Ser Ser Pro Ser
145                 150                 155                 160

Ser Gly Pro Lys Arg Tyr Asp Trp Thr Gly Lys Asn Trp Val Tyr Ser
                165                 170                 175

His Asp Gly Val Ser Leu His Glu Leu Leu Ala Ala Glu Leu Thr Lys
            180                 185                 190

Ala Leu Lys Thr Lys Leu Asp Leu Ser Ser Leu Ala Tyr Ser Gly Lys
            195                 200                 205

Asp Ala
    210

<210> SEQ ID NO 2
<211> LENGTH: 210
<212> TYPE: PRT
<213> ORGANISM: Macaca fascicularis

<400> SEQUENCE: 2

Met Trp Thr Phe Gly Arg Arg Ala Val Ala Gly Leu Leu Ala Ser Pro
1               5                   10                  15

Ser Pro Ala Gln Ala Gln Thr Leu Thr Arg Ala Pro Arg Leu Ala Glu
            20                  25                  30

Leu Ala Gln Leu Cys Ser Arg Arg Gly Leu Arg Thr Gly Ile Asn Ala
            35                  40                  45

Thr Arg Thr Thr His His Thr Ser Ser Asn Leu Arg Gly Leu Asn Gln
        50                  55                  60

Ile Arg Asn Val Lys Arg Gln Ser Val Tyr Leu Met Asn Leu Arg Lys
65                  70                  75                  80

Ser Gly Thr Leu Gly His Pro Gly Ser Leu Asp Asp Thr Thr Tyr Glu
                85                  90                  95

```
Arg Leu Ala Glu Glu Thr Leu Asp Ser Leu Ala Glu Phe Phe Glu Asp
            100                 105                 110
Leu Ala Asp Lys Pro Tyr Thr Phe Glu Asp Tyr Asp Val Ser Phe Gly
            115                 120                 125
Ser Gly Val Leu Thr Val Lys Leu Gly Gly Asp Leu Gly Thr Tyr Val
            130                 135                 140
Ile Asn Lys Gln Thr Pro Asn Lys Gln Ile Trp Leu Ser Ser Pro Ser
145                 150                 155                 160
Ser Gly Pro Lys Arg Tyr Asp Arg Thr Gly Lys Asn Trp Val Tyr Ser
                165                 170                 175
His Asp Gly Val Ser Leu His Glu Leu Leu Gly Ala Glu Leu Thr Lys
            180                 185                 190
Ala Leu Lys Thr Lys Leu Asp Leu Ser Ser Leu Ala Tyr Ser Gly Lys
            195                 200                 205
Asp Ala
    210

<210> SEQ ID NO 3
<211> LENGTH: 217
<212> TYPE: PRT
<213> ORGANISM: Bos taurus

<400> SEQUENCE: 3

Met Trp Thr Leu Gly Arg Arg Ser Val Ala Ser Phe Leu Pro Arg Ser
1               5                   10                  15
Ala Leu Pro Gly Phe Ala Pro Thr Arg Ala Gly Ala Pro Arg Pro Ala
            20                  25                  30
Lys Asp Leu Ser Leu Ser Gly Leu Pro Gly Leu Arg Ile Gly Thr Ala
            35                  40                  45
Lys Ala Pro Ala Arg Ser Gln Ser Ser Leu Ser Leu Arg Cys Leu Asn
        50                  55                  60
Gln Thr Leu Asp Val Lys Lys Gln Ser Val Cys Trp Ile Asn Leu Arg
65                  70                  75                  80
Thr Ala Gly Thr Leu Gly Asp Ala Gly Thr Leu Asp Asp Thr Thr Tyr
                85                  90                  95
Glu Arg Leu Ala Glu Glu Thr Leu Asp Ser Leu Ala Glu Phe Phe Glu
            100                 105                 110
Asp Leu Ala Asp Lys Pro Tyr Thr Phe Glu Asp Tyr Asp Val Ser Phe
            115                 120                 125
Gly Ser Gly Val Leu Thr Val Lys Leu Gly Gly Asp Leu Gly Thr Tyr
            130                 135                 140
Val Ile Asn Lys Gln Thr Pro Asn Lys Gln Ile Trp Leu Ser Ser Pro
145                 150                 155                 160
Ser Ser Gly Pro Lys Arg Tyr Asp Trp Thr Gly Arg Asn Trp Val Tyr
                165                 170                 175
Ser His Asp Gly Val Ser Leu His Glu Leu Leu Ala Thr Glu Leu Thr
            180                 185                 190
Gln Ala Leu Lys Thr Lys Leu Asp Leu Ser Ala Leu Ala Tyr Ser Gly
            195                 200                 205
Lys Asp Thr Cys Cys Pro Ala Gln Cys
    210                 215

<210> SEQ ID NO 4
<211> LENGTH: 211
<212> TYPE: PRT
<213> ORGANISM: Canis familiaris
```

<400> SEQUENCE: 4

```
Met Trp Thr Leu Gly Arg Arg Ala Ala Gly Leu Leu Pro Arg Ser
1               5                  10                  15

Ala Pro Pro Gly Ser Ala Ala Gly Ala Gly Thr Arg Gly Pro Thr
            20                  25                  30

Arg Ala Ala Pro Leu His Gly Arg Gly Leu Arg Val Gly Thr Gly
        35                  40                  45

Ala Ala Arg Gly Pro Ser His Ala Asn Leu Ser Leu His His Leu Asn
    50                  55                  60

Gln Leu Val Asn Val Lys Lys Gln Ser Val Cys Leu Met Asn Met Arg
65                  70                  75                  80

Thr Val Gly Thr Val Ser Ser Pro Gly Ser Leu Asp Glu Thr Thr Tyr
                85                  90                  95

Glu Arg Leu Ala Glu Thr Thr Leu Asp Ser Leu Ala Glu Phe Phe Glu
            100                 105                 110

Asp Leu Ala Asp Lys Pro Tyr Thr Leu Glu Asp Tyr Asp Val Ser Phe
        115                 120                 125

Gly Ser Gly Val Leu Thr Val Lys Leu Gly Gly Asp Leu Gly Thr Tyr
    130                 135                 140

Val Ile Asn Lys Gln Thr Pro Asn Lys Gln Ile Trp Leu Ser Ser Pro
145                 150                 155                 160

Ser Ser Gly Pro Lys Arg Tyr Asp Trp Thr Gly Lys Asn Trp Val Tyr
                165                 170                 175

Ser His Asp Gly Val Ser Leu His Glu Leu Leu Ala Thr Glu Leu Thr
            180                 185                 190

Lys Ala Phe Lys Ile Lys Leu Asp Leu Ser Ser Leu Ala Tyr Ser Gly
        195                 200                 205

Lys Gly Thr
    210
```

<210> SEQ ID NO 5
<211> LENGTH: 207
<212> TYPE: PRT
<213> ORGANISM: Mus musculus

<400> SEQUENCE: 5

```
Met Trp Ala Phe Gly Gly Arg Ala Ala Val Gly Leu Leu Pro Arg Thr
1               5                  10                  15

Ala Ser Arg Ala Ser Ala Trp Val Gly Asn Pro Arg Trp Arg Glu Pro
            20                  25                  30

Ile Val Thr Cys Gly Arg Arg Gly Leu His Val Thr Val Asn Ala Gly
        35                  40                  45

Ala Thr Arg His Ala His Leu Asn Leu His Tyr Leu Gln Ile Leu Asn
    50                  55                  60

Ile Lys Lys Gln Ser Val Cys Val Val His Leu Arg Asn Leu Gly Thr
65                  70                  75                  80

Leu Asp Asn Pro Ser Ser Leu Asp Glu Thr Ala Tyr Glu Arg Leu Ala
                85                  90                  95

Glu Glu Thr Leu Asp Ser Leu Ala Glu Phe Phe Glu Asp Leu Ala Asp
            100                 105                 110

Lys Pro Tyr Thr Leu Glu Asp Tyr Asp Val Ser Phe Gly Asp Gly Val
        115                 120                 125

Leu Thr Ile Lys Leu Gly Gly Asp Leu Gly Thr Tyr Val Ile Asn Lys
    130                 135                 140

Gln Thr Pro Asn Lys Gln Ile Trp Leu Ser Ser Pro Ser Ser Gly Pro
```

```
                145                 150                 155                 160
Lys Arg Tyr Asp Trp Thr Gly Lys Asn Trp Val Tyr Ser His Asp Gly
                    165                 170                 175

Val Ser Leu His Glu Leu Leu Ala Arg Glu Leu Thr Lys Ala Leu Asn
                180                 185                 190

Thr Lys Leu Asp Leu Ser Ser Leu Ala Tyr Ser Gly Lys Gly Thr
                195                 200                 205

<210> SEQ ID NO 6
<211> LENGTH: 169
<212> TYPE: PRT
<213> ORGANISM: Danio rerio

<400> SEQUENCE: 6

Met Ser Ser Gly Leu Asn Ser Ile Ser Gly Gly Arg Ser Val Ser Ser
1               5                   10                  15

Ala Asn Ile Cys Gly Arg His Thr Gln Cys Phe Asp Arg Ile Leu Asn
                20                  25                  30

Lys Arg Asp Leu His Leu Ser Gly Pro Leu Gly Glu Glu Lys Ala His
            35                  40                  45

His Leu Arg Glu Ile Ser Glu Ala Glu Tyr Glu Arg Leu Ala Glu Glu
        50                  55                  60

Thr Leu Asp Ala Leu Ala Asp Tyr Phe Glu Asp Leu Thr Asp Glu Asn
65                  70                  75                  80

Phe Thr Gly Leu Asp Tyr Asp Val Val Phe Ser Asn Gly Val Leu Thr
                85                  90                  95

Val Lys Val Gly Ser Asp His Gly Thr Tyr Val Ile Asn Lys Gln Thr
            100                 105                 110

Pro Asn Arg Gln Ile Trp Leu Ser Ser Pro Thr Ser Gly Pro Lys Arg
        115                 120                 125

Tyr Asp Trp Thr Gly Glu Arg Trp Val Tyr Thr His Asp Ala Val Pro
    130                 135                 140

Leu His Ser Leu Leu Ser Lys Glu Leu Ser Ile Ile Phe Lys Thr Asn
145                 150                 155                 160

Ile Asp Leu Ser His Leu Ile His Ser
                165

<210> SEQ ID NO 7
<211> LENGTH: 190
<212> TYPE: PRT
<213> ORGANISM: Drosophila melanogaster

<400> SEQUENCE: 7

Met Phe Ala Gly Arg Leu Met Val Arg Ser Ile Val Gly Arg Ala Cys
1               5                   10                  15

Leu Ala Thr Met Gly Arg Trp Ser Lys Pro Gln Ala His Ala Ser Gln
                20                  25                  30

Val Ile Leu Pro Ser Thr Pro Ala Ile Ala Ala Val Ala Ile Gln Cys
            35                  40                  45

Glu Glu Phe Thr Ala Asn Arg Arg Leu Phe Ser Ser Gln Ile Glu Thr
        50                  55                  60

Glu Ser Thr Leu Asp Gly Ala Thr Tyr Glu Arg Val Cys Ser Asp Thr
65                  70                  75                  80

Leu Asp Ala Leu Cys Asp Tyr Phe Glu Glu Leu Thr Glu Asn Ala Ser
                85                  90                  95

Glu Leu Gln Gly Thr Asp Val Ala Tyr Ser Asp Gly Val Leu Thr Val
            100                 105                 110
```

```
Asn Leu Gly Gly Gln His Gly Thr Tyr Val Ile Asn Arg Gln Thr Pro
            115                 120                 125

Asn Lys Gln Ile Trp Leu Ser Ser Pro Thr Ser Gly Pro Lys Arg Tyr
        130                 135                 140

Asp Phe Val Gly Thr Val Ala Ala Gly Arg Trp Ile Tyr Lys His Ser
145                 150                 155                 160

Gly Gln Ser Leu His Glu Leu Leu Gln Gln Glu Ile Pro Gly Ile Leu
                165                 170                 175

Lys Ser Gln Ser Val Asp Phe Leu Arg Leu Pro Tyr Cys Ser
                180                 185                 190

<210> SEQ ID NO 8
<211> LENGTH: 136
<212> TYPE: PRT
<213> ORGANISM: Caenorhabditis elegans

<400> SEQUENCE: 8

Met Leu Ser Thr Ile Leu Arg Asn Asn Phe Val Arg Ser Phe Ser
1               5                   10                  15

Ser Arg Ile Phe Ser Gln Asn Glu Tyr Glu Thr Ala Ala Asp Ser Thr
                20                  25                  30

Leu Glu Arg Leu Ser Asp Tyr Phe Asp Gln Ile Ala Asp Ser Phe Pro
            35                  40                  45

Val Ser Glu Gln Phe Asp Val Ser His Ala Met Gly Val Leu Thr Val
        50                  55                  60

Asn Val Ser Lys Ser Val Gly Thr Tyr Val Ile Asn Lys Gln Ser Pro
65                  70                  75                  80

Asn Lys Gln Ile Trp Leu Ser Ser Pro Met Ser Gly Pro Lys Arg Tyr
                85                  90                  95

Asp Leu Glu Glu Glu Gly Lys Trp Thr Tyr Ala His Asp Gly Glu Gln
            100                 105                 110

Leu Asp Ser Leu Leu Asn Arg Glu Phe Arg Lys Ile Leu Ala Asp Asp
        115                 120                 125

Arg Ile Asp Phe Ser Arg His Val
        130                 135

<210> SEQ ID NO 9
<211> LENGTH: 174
<212> TYPE: PRT
<213> ORGANISM: Saccharomyces cerevisiae

<400> SEQUENCE: 9

Met Ile Lys Arg Ser Leu Ala Ser Leu Val Arg Val Ser Ser Val Met
1               5                   10                  15

Gly Arg Arg Tyr Met Ile Ala Ala Ala Gly Gly Glu Arg Ala Arg Phe
                20                  25                  30

Cys Pro Ala Val Thr Asn Lys Lys Asn His Thr Val Asn Thr Phe Gln
            35                  40                  45

Lys Arg Phe Val Glu Ser Ser Thr Asp Gly Gln Val Val Pro Gln Glu
        50                  55                  60

Val Leu Asn Leu Pro Leu Glu Lys Tyr His Glu Glu Ala Asp Asp Tyr
65                  70                  75                  80

Leu Asp His Leu Leu Asp Ser Leu Glu Glu Leu Ser Glu Ala His Pro
                85                  90                  95

Asp Cys Ile Pro Asp Val Glu Leu Ser His Gly Val Met Thr Leu Glu
            100                 105                 110
```

```
Ile Pro Ala Phe Gly Thr Tyr Val Ile Asn Lys Gln Pro Pro Asn Lys
            115                 120                 125

Gln Ile Trp Leu Ala Ser Pro Leu Ser Gly Pro Asn Arg Phe Asp Leu
            130                 135                 140

Leu Asn Gly Glu Trp Val Ser Leu Arg Asn Gly Thr Lys Leu Thr Asp
145                 150                 155                 160

Ile Leu Thr Glu Glu Val Glu Lys Ala Ile Ser Lys Ser Gln
                165                 170
```

<210> SEQ ID NO 10
<211> LENGTH: 177
<212> TYPE: PRT
<213> ORGANISM: Candida sp.

<400> SEQUENCE: 10

```
Met Phe Lys Arg Phe Ala Leu Asn Thr Ala Lys Ala Leu Ser Lys Pro
1               5                   10                  15

Ala Tyr Ser Gln Gln Leu Ile Tyr Pro Gln Val Arg Phe Ile Thr Gln
            20                  25                  30

Thr Leu Pro Thr Val Ala Cys Gly Leu Arg Pro Leu Gly Ser Val Arg
        35                  40                  45

Thr Tyr Ser Leu Ser Thr Glu Gly Glu Ala Ile Asp Asp Lys Ile Asp
50                  55                  60

Lys Ile Thr Asp Asn Glu Tyr Ala Lys Val Ser Asn Glu Tyr Leu Glu
65                  70                  75                  80

Asn Leu Ser Asp Ser Leu Glu Glu Leu Asn Glu Asp Phe Glu Gln Val
                85                  90                  95

Asp Ser Glu Leu Ser Gln Gly Val Leu Thr Leu Thr Leu Pro Pro Asn
            100                 105                 110

Gly Thr Tyr Val Ile Asn Lys Gln Pro Pro Asn Lys Gln Ile Trp Leu
            115                 120                 125

Ser Ser Pro Ile Ser Gly Pro Lys Arg Tyr Asp Leu Ile Gly Gly Lys
        130                 135                 140

Trp Val Thr Leu Arg Asp Gly Ser Ser Leu Thr Ser Leu Leu Gln Glu
145                 150                 155                 160

Glu Ile Ser Ser Ala Ile Gly Gln Glu Phe Thr Phe Glu Asn Val Glu
                165                 170                 175

Gln
```

<210> SEQ ID NO 11
<211> LENGTH: 193
<212> TYPE: PRT
<213> ORGANISM: Dictyostelium sp.

<400> SEQUENCE: 11

```
Met Ile Phe Asn Phe Leu Asn Lys Ala Ser Asn Lys Thr His Thr Lys
1               5                   10                  15

Leu Leu Leu Phe Ser Ser Ile Arg Asn Arg Ile Leu Ile Asn Asn Ile
            20                  25                  30

Ser Ser Thr Ser Lys Trp Ser Ile Asn Asn Asn Lys Gln Ser
        35                  40                  45

Ser Val Ser Lys Thr Asn Ile Phe Ile Thr Thr His Asn Lys Gln
50                  55                  60

Gln Gln Gln Leu Ser Lys Ser Phe Ser Thr Ile Asn Asn Asn Thr Lys
65                  70                  75                  80

Pro Ile Ser Asp Val Asn Leu Phe His Asp Ile Val Asp Glu Glu Phe
                85                  90                  95
```

```
Glu Leu Phe Val Asp Arg Leu Glu Ile Leu Ser Glu Ala Asn Thr Cys
                100                 105                 110
Glu Gly Phe Glu Val Glu Gly Asn Asp Gly Val Leu Thr Ile Ile Val
            115                 120                 125
Gly Asn Lys Gly Thr Tyr Val Ile Asn Lys Gln Thr Pro Asn Arg Gln
130                 135                 140
Ile Trp Trp Ser Ser Pro Leu Ser Gly Pro Lys Arg Phe Asp Tyr Asp
145                 150                 155                 160
Ser Val Glu Lys Arg Trp Val Asp Asn Arg Asp Gly Thr Pro Leu Arg
                165                 170                 175
Gln Leu Leu Asn Ser Glu Ile Asn Thr Leu Cys Lys Tyr Asp Met Glu
            180                 185                 190
Ile

<210> SEQ ID NO 12
<211> LENGTH: 187
<212> TYPE: PRT
<213> ORGANISM: Arabidopsis thaliana

<400> SEQUENCE: 12

Met Ala Thr Ala Ser Arg Phe Leu Leu Arg Lys Leu Pro Arg Phe Leu
1               5                   10                  15
Lys Leu Ser Pro Thr Leu Leu Arg Ser Asn Gly Val Arg Val Ser Ser
                20                  25                  30
Asn Leu Ile Gln Asp Ser Ile Glu Pro Leu Asp Ser Phe Trp Arg Ile
            35                  40                  45
Gly Ser Arg Ile Arg His Asp Ser Leu Thr Thr Arg Ser Phe Ser Ser
        50                  55                  60
Gln Gly Pro Ala Ser Val Asp Tyr Ser Ser Val Leu Gln Glu Glu Glu
65                  70                  75                  80
Phe His Lys Leu Ala Asn Phe Thr Ile Asn His Leu Leu Glu Lys Ile
                85                  90                  95
Glu Asp Tyr Gly Asp Asn Val Gln Ile Asp Gly Phe Asp Ile Asp Tyr
                100                 105                 110
Gly Asn Glu Val Leu Thr Leu Lys Leu Gly Ser Leu Gly Thr Tyr Val
            115                 120                 125
Leu Asn Lys Gln Thr Pro Asn Arg Gln Ile Trp Met Ser Ser Pro Val
130                 135                 140
Ser Gly Pro Ser Arg Phe Asp Trp Asp Arg Asp Ala Asn Ala Trp Ile
145                 150                 155                 160
Tyr Arg Arg Thr Glu Ala Lys Leu His Lys Leu Leu Glu Glu Glu Leu
                165                 170                 175
Glu Asn Leu Cys Gly Glu Pro Ile Gln Leu Ser
            180                 185

<210> SEQ ID NO 13
<211> LENGTH: 199
<212> TYPE: PRT
<213> ORGANISM: Zea sp.

<400> SEQUENCE: 13

Met Ala Ser Arg Lys Leu Leu Val Gly Leu Thr Ala Arg Arg Gln Leu
1               5                   10                  15
Gln Ser Arg Thr Gln Gln Leu Phe Trp Ala Thr Ser Leu Pro Glu Ala
                20                  25                  30
Thr Thr Ser Arg Ser Leu Met Val Ala Ala Ala Met Ala Arg Leu Ser
```

```
            35                  40                  45
Asp Arg Ser Ser Ala Pro Phe Ile Leu Ser Ser Arg Ala Ile Ser Ser
 50                  55                  60

Thr Gln Pro Val Met Gln Ser Thr Gly Asp Val Ser Gly Ser Ser Pro
 65                  70                  75                  80

Ser Ala Val Asp His Lys Leu Ala Met Gln Glu Asp Glu Phe His Lys
                 85                  90                  95

Leu Ala Asp Glu Thr Ile His Asp Leu Leu Glu Lys Leu Glu Glu Tyr
                100                 105                 110

Gly Asp Ser Ile Gln Met Asp Gly Phe Asp Ile Glu Tyr Gly Asn Gln
                115                 120                 125

Val Leu Thr Leu Arg Leu Gly Asp Leu Gly Thr Tyr Val Ile Asn Lys
130                 135                 140

Gln Thr Pro Asn Lys Gln Ile Trp Leu Ser Ser Pro Val Ser Gly Pro
145                 150                 155                 160

Ser Arg Phe Asp Trp Asp Ala Thr Ala Asn Gly Trp Ile Tyr Lys Arg
                165                 170                 175

Thr Gly Val Asn Leu Val Arg Leu Leu Glu Lys Glu Ile Gly Glu Leu
                180                 185                 190

Cys Gly Thr Pro Val Glu Leu
                195

<210> SEQ ID NO 14
<211> LENGTH: 158
<212> TYPE: PRT
<213> ORGANISM: Schizosaccharomyces pombe

<400> SEQUENCE: 14

Met Gln Ser Leu Arg Ala Ala Phe Arg Arg Thr Pro Ile Phe Leu
 1               5                  10                  15

Lys Pro Tyr Glu Phe Ser Thr Asn Val Phe Gly Leu Arg Cys Arg Tyr
                 20                  25                  30

Tyr Ser Gln Val Arg His Asn Gly Ala Leu Thr Asp Leu Glu Tyr His
                 35                  40                  45

Arg Val Ala Asp Asp Thr Leu Asp Val Leu Asn Asp Thr Phe Glu Asp
 50                  55                  60

Leu Leu Glu Glu Val Gly Lys Lys Asp Tyr Asp Ile Gln Tyr Ala Asn
 65                  70                  75                  80

Gly Val Ile Thr Leu Met Leu Gly Glu Lys Gly Thr Tyr Val Ile Asn
                 85                  90                  95

Lys Gln Pro Pro Ala His Gln Ile Trp Leu Ser Ser Pro Val Ser Gly
                100                 105                 110

Pro Lys His Tyr Glu Tyr Ser Leu Lys Ser Lys Thr Trp Cys Ser Thr
                115                 120                 125

Arg Asp Glu Gly Thr Leu Leu Gly Ile Leu Ser Ser Glu Phe Ser Lys
130                 135                 140

Trp Phe Ser Arg Pro Ile Glu Phe Lys Lys Ser Glu Asp Phe
145                 150                 155

<210> SEQ ID NO 15
<211> LENGTH: 173
<212> TYPE: PRT
<213> ORGANISM: Cryptococcus neoformans

<400> SEQUENCE: 15

Met Leu Ala Ala Lys Asn Cys Leu Asn Lys Ser Leu Arg Ala Leu Arg
 1               5                  10                  15
```

```
Pro Leu Thr Glu Arg Ser Ala Ser Pro Val Ile Ala Arg Ser Ala Arg
                20                  25                  30

Ala Ser Pro Leu Leu Arg Ser Arg Ala Thr Ser Ala Arg Thr Pro Pro
            35                  40                  45

Thr Ser Thr Leu Ser His Asp Glu Tyr Glu His Val Ser Glu Arg Asp
        50                  55                  60

Met Glu Thr Leu Asn Glu Ser Leu Glu Ile Phe Cys Glu Asp Phe Gly
65                  70                  75                  80

Asn Gly Asn Trp Glu Ile Glu Tyr Ser Ser Gly Val Leu Asn Leu Thr
                85                  90                  95

Leu Pro Pro Tyr Gly Thr Tyr Val Leu Asn Lys Gln Pro Pro Asn Leu
            100                 105                 110

Gln Ile Trp Met Ser Ser Pro Val Ser Gly Pro Ser Arg Phe Glu Tyr
            115                 120                 125

Ile Asn Gly Ser Trp Val His His Arg Lys Glu Gly Val Lys Leu Gly
130                 135                 140

Glu Leu Leu Ser Gly Glu Leu Lys Glu Ile Leu Glu Lys Ser Gly Asn
145                 150                 155                 160

Glu Ala Ala Ala Gly Val Trp Asp Gly Val Gly Leu Pro
                165                 170

<210> SEQ ID NO 16
<211> LENGTH: 180
<212> TYPE: PRT
<213> ORGANISM: Trypanosoma sp.

<400> SEQUENCE: 16

Met Arg Arg Thr Cys Cys Ala Thr Thr Ser Ala Val Leu Arg Ser Leu
1               5                   10                  15

Val Tyr Leu Arg Pro His Gly Arg Ala Lys Pro Thr Thr Ser Gly Ser
                20                  25                  30

Gly Arg Lys Glu Arg Gln Phe Ser Thr Thr Thr Ala Arg Cys Glu Ser
            35                  40                  45

Lys Gly Trp His Pro Ala Lys Leu Gly Met Asp Gly Phe Thr Asp Val
        50                  55                  60

Ala Tyr Asn Thr Ala Ala Asp Thr Phe Leu Glu Arg Val Glu Ser Ala
65                  70                  75                  80

Leu Glu Thr Ile Gly Asp Thr Asp Thr Leu Glu Asp Val Asn Leu Ala
                85                  90                  95

Gly Gly Val Leu Val Ile Glu Thr Thr Ser Arg Gly Thr Phe Val Leu
            100                 105                 110

Asn Lys Gln Ala Pro Asn Val Gln Leu Trp Leu Ser Ser Pro Leu Ser
            115                 120                 125

Gly Pro His His Tyr Asp Met Thr Thr Ser Ala Thr Gly Ser Val Glu
130                 135                 140

Trp Arg Ala Asp Ala Asp Gly His Ser Leu Glu Glu Arg Leu Glu Lys
145                 150                 155                 160

Glu Leu Ser Asp Val Val Gly Thr Glu Val Ser Leu Ser Ser Gly Ala
                165                 170                 175

Gly Glu Thr Glu
            180
```